US009840704B2

(12) United States Patent
Dugast-Darzacq et al.

(10) Patent No.: US 9,840,704 B2
(45) Date of Patent: Dec. 12, 2017

(54) MOLECULAR TARGETS FOR THE PREVENTION AND/OR TREATMENT OF FIBROSIS, HYPERTROPHIC SCARS OR KELOIDS

(71) Applicants: Centre National de la Recherche Scientifique—CNRS, Paris (FR); INSERM (Institut National de la Sante et de la Recherche Medicale), Paris (FR); URGO RECHERCHE INNOVATION ET DEVELOPPEMENT, Chenove (FR); Universite Paris Diderot-Paris 7, Paris (FR); Ecole Normale Superieure, Paris (FR)

(72) Inventors: Claire Dugast-Darzacq, Antony (FR); Maite Noizet, Versailles (FR); Xavier Darzacq, Antony (FR)

(73) Assignees: Centre National de la Recherche Scientifique-CNRS CNRS, Paris (FR); INSERM (INSTITUT NATIONAL DE LA SANTÉ ET DE LA RECHERCHE MÉDICALE), Paris (FR); URGO RECHERCHE INNOVATION ET DEVELOPPEMENT, Chenove (FR); UNIVERSITÉ PARIS DIDEROT—PARIS 7, Paris (FR); ECOLE NORMALE SUPERIEURE, Paris (FR)

( * ) Notice: Subject to any disclaimer, the term of this patent is extended or adjusted under 35 U.S.C. 154(b) by 0 days.

(21) Appl. No.: 14/909,626

(22) PCT Filed: Jul. 30, 2014

(86) PCT No.: PCT/EP2014/066342
§ 371 (c)(1),
(2) Date: Feb. 2, 2016

(87) PCT Pub. No.: WO2015/018698
PCT Pub. Date: Feb. 12, 2015

(65) Prior Publication Data
US 2016/0168565 A1 Jun. 16, 2016

Related U.S. Application Data

(63) Continuation of application No. PCT/IB2013/001989, filed on Aug. 5, 2013.

(51) Int. Cl.
C12N 15/11 (2006.01)
A61K 31/715 (2006.01)
A61K 48/00 (2006.01)
C07H 21/02 (2006.01)
C07H 21/04 (2006.01)
C12N 15/113 (2010.01)
C07K 14/47 (2006.01)
A61K 45/06 (2006.01)
A61K 31/713 (2006.01)

(52) U.S. Cl.
CPC .......... *C12N 15/113* (2013.01); *A61K 31/713* (2013.01); *A61K 45/06* (2013.01); *C07K 14/4702* (2013.01); *C12N 2310/14* (2013.01); *C12N 2320/12* (2013.01); *C12N 2320/30* (2013.01)

(58) Field of Classification Search
None
See application file for complete search history.

(56) References Cited

FOREIGN PATENT DOCUMENTS

WO 2009/085274 7/2009

OTHER PUBLICATIONS

Yang et al (J. Clin. Invest 122(4): 1271-1282, 2012).*
Baum et al (J Cardiovasc Pharmacol. Apr. 2011; 57(4): 376-379).*
Yang et al (Hepatology 2009;49:1982-1991).*
Yang et al (Hepatology 2010;51:1291-1301).*
Desmouliére et al., "Transforming Growth Factor-β1 Induces α-Smooth Muscle Actin Expression in Granulation Tissue Myofibroblasts and in Quiescent and Growing Cultured Fibroblasts", The Journal of Cell Biology, vol. 122, No. 1, Jul. 1993, 103-111.
International Search Report in PCT/EP2014/066342 dated Dec. 15, 2014.
Jennifer M. Hahn et al., "Keloid-derived keratinocytes exhibit an abnormal gene expression profile consistent with a distinct causal role in keloid pathology," Wound Repair and Regeneration, 21(4):530-544 (2013) XP055112583.
Jerome Avouac et al., "Inactivation of the transcription factor STAT-4 prevents inflammation-driven fibrosis in animal models of systemic sclerosis," Arthritis & Rheumatism, 63(3):800-809 (2011) XP0055112868.
Tao Ling et al., "Role of the JAK-STAT pathway in proliferation and differentiation of human hypertrophic scar fibroblasts induced by connective tissue growth factor," Mol. Med. Reports, 3(6):941-945 (2010) XP002722998.
Ying-Mei Lin et al., "HIC1 interacts with and modulates the activity of STAT3," Cell Cycle, 12(14):2266-2276 (2013) KP055143038.

* cited by examiner

*Primary Examiner* — Richard Schnizer
(74) *Attorney, Agent, or Firm* — McAndrews, Held & Malloy, Ltd.

(57) ABSTRACT

The present invention relates to a therapeutic compound comprising: an agent that inhibits the activity of at least one gene selected from the group consisting of HIC1, FOXS1, CREB5, IRF7, POU2F2, STAT4, TCF4, and/or an agent that enhances the activity of at least one gene selected from the group consisting of MAF, MEOX2, SIX2.

12 Claims, 13 Drawing Sheets

FIG. 1B

Figure 1A:
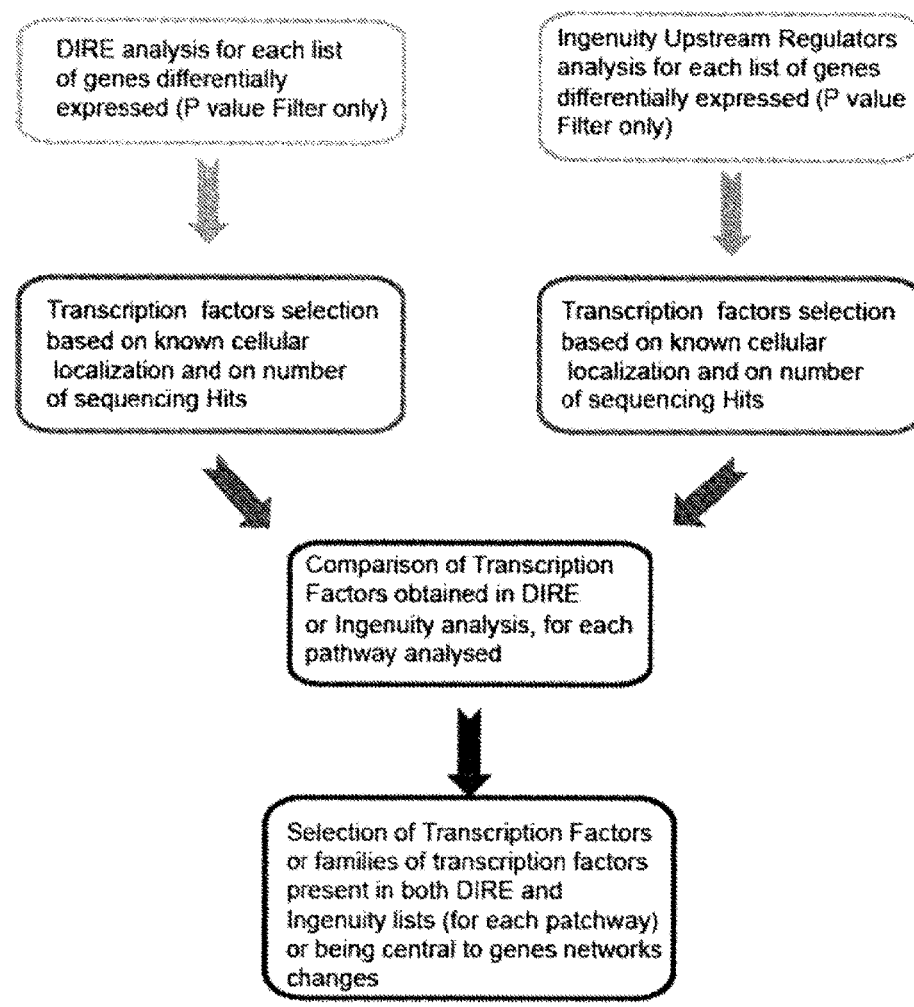

| Symbol | Entrez Gene Name |
|---|---|
| CREB5 | cAMP_responsive_element_binding_protein_5 |
| E2F1 | E2F_transcription_factor_1 |
| EGR2 | early_growth_response_2 |
| ETS1 | v-ets_erythroblastosis_virus_E26_oncogene_homolog_1_(avian) |
| FOXS1 | forkhead_box_S1 |
| GLI1 | GLI_family_zinc_finger_1 |
| HIC1 | hypermethylated_in_cancer_1 |
| IRF7 | interferon_regulatory_factor_7 |
| JUN | jun_oncogene |
| MAF | v-maf_musculoaponeurotic_fibrosarcoma_oncogene_homolog_(avian) |
| MEOX2 | Mesenchyme_homeobox_2 |
| MYC | v-myc_myelocytomatosis_viral_oncogene_homolog_(avian) |
| POU2F2 | POU_class_2_homeobox_2 |
| PPARG | peroxisome_proliferator-activated_receptor_gamma |
| SIX2 | SIX_homeobox_2 |
| SMAD3 | SMAD_family_member_3 |
| SMAD4 | SMAD_family_member_4 |
| SOX9 | SRY_(sex-determining_region_Y)-box_9 |
| SRF | serum_response_factor_(c-fos_serum_response_element-binding_transcription_factor) |
| STAT1 | signal_transducer_and_activator_of_ transcription_1_91kDa |
| STAT4 | signal_transducer_and_activator_of_ transcription_4 |
| TCF4 | transcription_factor_4 |
| USF2 | upstream_transcription_factor_2_c-fos_interacting |

FIG. 6

Table 1

| CREB5 | To decrease |
|---|---|
| E2F1 | To decrease |
| EGR2 | To decrease |
| ETS1 | To increase |
| FOXS1 | To increase |
| GLI1 | To decrease |
| HIC1 | To decrease |
| IRF7 | To decrease |
| JUN | To decrease |
| MAF | To increase |
| MEOX2 | To increase |
| MYC | To decrease |
| POU2F2 | To decrease |
| PPARG | To increase |
| SIX2 | To increase |
| SMAD3 | To decrease |
| SMAD4 | To decrease |
| SOX9 | To decrease |
| SRF | To decrease |
| STAT1 | To increase |
| STAT4 | To decrease |
| TCF4 | To decrease |
| USF2 | To decrease |

FIG. 7A

Table 2

| | | | |
|---|---|---|---|
| CREB5 | CCGGCGAAGGGUGGUAGACGA | Q, SI04157174 | 11 |
| | AACAGUAUUCUGUAGGAUCUA | Q, SI04141893 | 12 |
| E2F1 | UCGGAGAACUUUCAGAUCU | T, L-003259-00 | 13 |
| | GAGAAGUCACGCUAUGAGA | | 14 |
| | GAGCAGAUGGUUAUGGUGA | | 15 |
| | GAACAGGGCCACUGACUCU | | 16 |
| EGR2 | GAAGGCAUAAUCAAUAUUG | T, L-006527-00 | 17 |
| | CUACUGUGGCCGAAAGUUU | | 18 |
| | GAAACCAGACCUUCACUUA | | 19 |
| | GAGAAGAGGUCGUUGGAUC | | 20 |
| FOXS1 | AGGGCCAAUAAAGCCAUGUGA | Q, SI04152540 | 21 |
| | CUGGCUCUAGGACCUGAAGAA | Q, SI00387527 | 22 |
| GLI1 | GCAAAUAGGGCUUCACAUA | T, L-003896-00 | 23 |
| | AGGCUCAGCUUGUGUGUAA | | 24 |
| | GGACGAGGGACCUUGCAUU | | 25 |
| | CAGCUAGAGUCCAGAGGUU | | 26 |
| HIC1 | GCACAGCAACGCAACCUCA | T, L-006532-00 | 27 |
| | GAGCUUCGGUGACAACCUG | | 28 |
| | UGAUCAUCGUGGUGCAGAA | | 29 |
| | GACCAUCGACCGUUUCUCU | | 30 |
| IRF7 | GCACAAGGUGUACGCGCUC | T, L-011810-00 | 31 |
| | CAACUUCCGCUGCGCACUG | | 32 |
| | GCGCGCAUCUUCAAGGCCU | | 33 |
| | CAGGCACGGACCAGACUGA | | 34 |
| JUN | GAGCGGACCUUAUGGCUAC | T, L-003268-00 | 35 |
| | GAACAGGUGGCACAGCUUA | | 36 |
| | GAAACGACCUUCUAUGACG | | 37 |
| | UGAAAGCUCAGAACUCGGA | | 38 |
| MAF | UUCGAUCUGAUGAAGUUUGAA | Q, SI00076048 | 1 |
| | CGGCAGGAGAAUGGCAUCAGA | Q, SI03086069 | 2 |
| MEOX2 | AGCAUGCGCACUUAUGAUAUA | Q, SI04299421 | 3 |
| | CCCGCCCGUCCUGUGCUCCAA | Q, SI04262174 | 4 |
| MYC | ACGGAACUCUUGUGCGUAA | T, L-003282-00 | 39 |
| | GAACACACAACGUCUUGGA | | 40 |
| | AACGUUAGCUUCACCAACA | | 41 |
| | CGAUGUUGUUUCUGUGGAA | | 42 |
| PPARγ | UCCGGAGAACAAUCAGAUUGA | Q, SI03115266 | 5 |
| | GAGGGCGAUCUUGACAGGAAA | Q, SI00071673 | 6 |
| SIX2 | CAACGAGAACUCCAAUUCUAA | Q, SI00719313 | 7 |
| | CCCGCUGAAUGGCAGCGGCAA | Q, SI04141095 | 8 |
| SMAD3 | CAACAGGAAUGCAGCAGUG | T, L-020067-00 | 43 |
| | GAGUUCGCCUUCAAUAUGA | | 44 |
| | GGACGCAGGUUCUCCAAAC | | 45 |
| | UUAGAGACAUCAAGUAUGG | | 46 |

FIG. 7B

| | | | |
|---|---|---|---|
| SMAD4 | GCAAUUGAAAGUUUGGUAA | T, L-003902-00 | 47 |
| | CCCACAACCUUUAGACUGA | | 48 |
| | GAAUCCAUAUCACUACGAA | | 49 |
| | GUACAGAGUUACUACUUAG | | 50 |
| SOX9 | GGAACAACCCGUCUACACA | T, L-021507-00 | 51 |
| | GAACAAGCCGCACGUCAAG | | 52 |
| | GACCUUCGAUGUCAACGAG | | 53 |
| | GGAAGUCGGUGAAGAACGG | | 54 |
| SRF | UGAGACAGGCCAUGUGUAU | T, L-009800-00 | 55 |
| | GGACUGUGCUGAAGAGUAC | | 56 |
| | GCACCAAGAGUGAAUGAUC | | 57 |
| | GCACCAGUGUCUGCUAGUG | | 58 |
| STAT1 | GCACGAUGGGCUCAGCUUU | T, L-003543-00 | 59 |
| | CUACGAACAUGACCCUAUC | | 60 |
| | GAACCUGACUUCCAUGCGG | | 61 |
| | AGAAAGAGCUUGACAGUAA | | 62 |
| STAT4 | GAACUAAACUAUCAGGUAA | T, L-011784-00 | 63 |
| | GCAUGUAGCUGUGGUUAUU | | 64 |
| | CAAUCUAGCUACAGUGAUG | | 65 |
| | CUGCGAGACUACAAAGUUA | | 66 |
| TCF4 | GCACUUGCUUCGAUCUAUU | T, L-004594-00 | 67 |
| | GACAAAGAGCUGAGUGAUU | | 68 |
| | GCACAGCUGUUUGGUCUAG | | 69 |
| | CAACGGGACAGACAGUAUA | | 70 |
| USF2 | GCAAGACGGGAGCGAGUAA | T, L-003618-00 | 71 |
| | GGAGGGACAAGAUCAACAA | | 72 |
| | GAAGAGCCCAGCACAACGA | | 73 |
| | CAAAAUCCCUUCAGCAAUG | | 74 |

MOLECULAR TARGETS FOR THE PREVENTION AND/OR TREATMENT OF FIBROSIS, HYPERTROPHIC SCARS OR KELOIDS

The present application is filed pursuant to 35 U.S.C. 371 as a U.S. National Phase application of International Patent Application No. PCT/EP2014/066342, which was filed Jul. 30, 2014, claiming the benefit of priority to International Patent Application No. PCT/IB2013/001989, which was filed on Aug. 5, 2013. The entire text of the aforementioned applications is incorporated herein by reference in its entirety.

FIELD OF THE INVENTION

The present invention relates to at least one molecular target for the prevention and/or treatment of fibrosis, hypertrophic scars or keloids. Further, the invention concerns a novel therapeutic for preventing or treating fibrosis, hypertrophic scars or keloids and a novel gene therapy approach, involving said molecular target for preventing and/or treating said fibrosis, hypertrophic scars or keloids. Additionally, the invention concerns a method for preventing and/or treating fibrosis, hypertrophic scars or keloids using said therapeutic or said gene therapy.

BACKGROUND OF THE INVENTION

Fibrosis is the formation of excess fibrous tissues or scar tissue in an organ or a tissue. Fibrosis is a common pathophysiological response of tissues to chronic injury or long-term inflammation. There are many potential origins of this fibrosis. It can be induced by a disease (inherited or not), by side effects of a treatment (for example radiation or chemotherapy), by a toxic environment (for example smoking), or by an injury. It can affect different organs such as the skin or the lung.

Fibrosis induced generally the failure of the tissue of the organ that is affected. Fibrotic tissue is like a scar tissue, stiff, thick, and rigid. Sometimes, it can also swell. For example, in the lung, fibrosis lead to a shortness of breath particularly during exercise and dry and hacking cough, due to the abnormal expansion of the fibrosis lung.

Some examples of fibrosis are pulmonary fibrosis (lungs), cystic fibrosis (lung and digestive system), Crohn's Disease (intestine), scleroderma/systemic sclerosis (lungs or skin), arthrofibrosis (knee, shoulder, other joints), cutaneous fibrosis with hypertrophic or keloid scars When the tissue concerned by this phenomenon is the skin, it is principally the wound healing process that is affected.

The natural wound healing is divided into three sequential phases; each phase is characterized by specific cellular activities: the inflammatory phase, the proliferative phase and the remodeling phase.

The first phase, called the inflammatory phase, begins minutes after injury. The blood vessels rupture induces the clot formation, composed mainly of fibrin and fibronectin. The clot fills partially the lesion and allows the migration of the inflammatory cells within the lesion. The inflammatory cells are recruited to debride the wound. Platelets secrete factors, such as growth factors or cytokines, which induce the recruitment of cells implicated in the wound healing (inflammatory cells such as neutrophils and macrophages, fibroblasts and endothelial cells).

The second phase is called the proliferative phase and corresponds to the development of the granulation tissue. Fibroblasts migrate into the wound area, proliferate and form a new provisional extracellular matrix by secreting extracellular matrix (ECM) proteins. Then endothelial cells migrate to promote the neovascularization or angiogenesis of the lesion. Inside the granulation tissue, fibroblasts activate and differentiate into myofibroblasts, presenting contractile properties thanks to their expression of alpha-smooth muscle actin (similar to that in smooth muscle cells). Myofibroblasts have a key role in wound healing as they provide the contraction of the wound. Finally, keratinocytes migrate from the wound edge, proliferate and differentiate to reconstitute the epidermis.

The last phase of the wound healing process appears after the wound closure. It corresponds to the remodeling of the granulation tissue. The granulation tissue is reorganized, type III collagen is replaced by type I collagen, as normal dermis is principally composed of type I collagen. During this phase, myofibroblasts in excess are eliminated by apoptosis. The last phase of the wound healing is long. One year after injury, the scar is remodeled; it gets less red and thinner.

However, this process is not only complex but fragile; it is susceptible to interruption or failure leading to the formation of chronic or non-healing wounds or formation of abnormal scars. Factors which may contribute to this include diseases (such as diabetes, venous or arterial disease), age, infection or tissue localization.

Role of Fibroblasts in Wound Healing

Fibroblasts are implicated in the process of wound healing, this involves several steps of differentiation from a quiescent fibroblast to a mobilized fibroblast that will transform into a myofibroblast and finally enter apoptosis.

In normal wound healing, fibroblasts get activated, and then differentiate into myofibroblasts presenting contractile properties thanks to their expression of alpha-smooth muscle actin ($\alpha$SMA). Myofibroblasts are responsible for the deposit of extra cellular matrix and for the wound closure by moving closer the wound edges. In hypertrophic scar, keloid or fibrous wound healing, the activity of myofibroblasts persists and leads to tissue deformation, which is particularly evident, for example, in hypertrophic scars developed after burn injury. The aim of the present invention is to map, at the whole genome scale, the different genes that will be activated or deactivated during this process, and thus providing a molecular signature of abnormal healing leading to abnormal scar or fibrosis Connective tissues represent a wide variety of physical structures and different functions: tendons, cartilage, bone, dermis, cornea, etc. . . . As organs and tissues have specific functions (for example, skin functions are protection, sensation and heat regulation), connective tissues constituting these tissues and organs have also precise functions provided by specific cell types. For example, in the papillar or reticular dermis collagen I, III and V, XIV, elastic fibers, perlecan or SPARC are found On the contrary, types III, IX, X collagens are found associated with aggregan and dermatan sulfate in tendons.

Fibroblasts are the main cells of connective (or mesenchymal) tissues, in which cells are surrounded by extracellular matrix (contrary to epithelium where they are jointed together). These fibroblasts are active in wound healing of damages organs, as they proliferate, differentiate in myofibroblast, secrete collagens and other specific ECM proteins and fibers composing the connective tissue of the organ, leading to the healing and reorganization of the tissue.

Myofibroblasts are defined as the primary source of the excessive ECM proteins deposition occurring during fibrosis. Resident myofibroblasts arise from a population of tissue specific fibroblasts that proliferate and undergo activation in response to injury, as it is the case in many organs such as skin, lungs, or kidney.

Fibrosis, Hypertrophic Scars and Keloids

Fibrosis is a common pathophysiological response of tissues to chronic injury. Fibrosis affects different organs such as the skin or the lung. Fibrosis is characterized by a differentiation of fibroblasts into myofibroblasts and an excessive accumulation of connective tissue. Fibrosis induces a loss of function of the organ and potentially the failure of the organ.

Hypertrophic, keloid or fibrous scars result from abnormal wound healing. These scars are characterized by an excessive deposit of ECM proteins, especially collagen. In these abnormal wounds, granulation tissue is hyper proliferative, due to an excess of myofibroblasts (<<Cellular and molecular pathology of HTS: basis for treatment.>> Armour A, Scott P G, Tredget E E. Wound Repair Regen. 2007 September-October; 15 Suppl 1:S6-17. Review. Erratum in: Wound Repair Regen. 2008 July-August; 16(4):582).

In normal wound healing, fibroblasts get activated, and then differentiate into myofibroblasts presenting contractile properties thanks to their expression of alpha-smooth muscle actin (αSMA). Myofibroblasts are responsible for the deposit of extra cellular matrix and for the wound closure by moving closer the wound edges. In hypertrophic scar, keloid or fibrous wound healing, the activity of myofibroblasts persists and leads to tissue deformation, which is particularly evident, for example, in hypertrophic scars developed after burn injury.

Hypertrophic and keloid scars are characterized by deposit of excessive amounts of collagen leading to a raised scar (more intense in keloids than in hypertrophic scars). They are formed most often at the sites of pimples, body piercings, cuts and burns.

Some hypertrophic scars are non-functional scars as they limit the function of the skin where they developed. They generate a loss of mobility of the scar zone and the neighboring zones, which can completely limit the movements (for example, elbow and mobility of the arm). They are mostly the result of burns of specific anatomical zones.

Thus, the treatment of the wound is especially adapted to the wound in its early stage if it presents a risk of developing an abnormal scar or failing to heal correctly. By enhancing or manipulating factors that contribute to wound healing it may therefore be possible to correct the process, thereby reducing the likely occurrence of a fibrosis, hypertrophic scar or keloid. If a tissue (of an organ for example) is susceptible of developing a fibrosis, the treatment of this tissue at an early stage is also of interest.

The present invention can improve the quality of a patient's life by ensuring that new wounds do not deteriorate into a fibrosis, hypertrophic scar or keloid and existing wounds can be treated in a way that actively promotes healing and by the way prevents the formation of fibrosis, hypertrophic scar or keloid.

SUMMARY OF THE INVENTION

In one aspect, the present invention relates to a therapeutic compound comprising:
  an agent that inhibits the activity of at least one gene selected from the group consisting of HIC1, FOXS1, CREB5, IRF7, POU2F2, STAT4, TCF4, preferentially TCF4, FOXS1, STAT4
  and/or
  an agent that enhances the activity of at least one gene selected from the group consisting of MAF, MEOX2, SIX2
  for use in the prevention and/or treatment of fibrosis, hypertrophic scar or keloid.

The present invention also relates to a pharmaceutical composition comprising a therapeutic compound as defined above together with a pharmaceutically acceptable carrier.

The invention also relates to a method for preparing a pharmaceutical composition as described above comprising bringing said therapeutic compound in conjunction or association with a pharmaceutically or veterinary acceptable carrier or vehicle.

In one aspect, the invention relates to a method for treating or preventing mammalian fibrosis, hypertrophic scar or keloid wherein said method comprises administering to said fibrosis, hypertrophic scar or keloid or tissue susceptible of developing fibrosis, hypertrophic scar or keloid a therapeutic compound comprising:
  an agent that inhibits the activity of at least one gene selected from the group consisting of HIC1, FOXS1, CREB5, IRF7, POU2F2, STAT4, TCF4, preferentially TCF4, FOXS1, STAT4
  and/or
  an agent that enhances the activity of at least one gene selected from the group consisting of MAF, MEOX2, SIX2.

In another aspect, the invention relates to a kit for treating a fibrosis, hypertrophic scar or keloid or tissue susceptible of developing fibrosis, hypertrophic scar or keloid wherein said kit comprises:
  (a) at least one therapeutic compound or composition as defined above and
  (b) at least one dressing for applying to said wound.

The invention also relates to a combination therapeutic for treating a fibrosis, hypertrophic scar or keloid or tissue susceptible of developing fibrosis, hypertrophic scar or keloid comprising:
  (a)—an agent that inhibits the activity of at least one gene selected from the group consisting of HIC1, FOXS1, CREB5, IRF7, POU2F2, STAT4, TCF4, preferentially TCF4, FOXS1, STAT4
  and/or
  an agent that enhances the activity of at least one gene selected from the group consisting of MAF, MEOX2, SIX2
  and
  b) at least one further therapeutic.

In yet another aspect, the invention relates to the use of:
  an agent that inhibits the activity of at least one gene selected from the group consisting of HIC1, FOXS1, CREB5, IRF7, POU2F2, STAT4, TCF4, preferentially TCF4, FOXS1, STAT4
  and/or
  an agent that enhances the activity of at least one gene selected from the group consisting of MAF, MEOX2, SIX2 for treating fibrosis, hypertrophic scar or keloid or tissue susceptible of developing fibrosis, hypertrophic scar or keloid
wherein said agent modulates fibroblast and myofibroblast differentiation and/or activity

DETAILED DESCRIPTION OF THE INVENTION

Accordingly, in one aspect of the invention there is provided a therapeutic compound comprising:
(a) an agent that inhibits the activity of at least one gene selected from the group consisting of:
HIC1, FOXS1, CREB5, IRF7, POU2F2, STAT4, TCF4 preferentially TCF4, FOXS1, STAT4
an agent that enhances the activity of at least one gene selected from the group consisting of MAF, MEOX2, SIX2
for use in the prevention and/or treatment of fibrosis, hypertrophic scars or keloids.

In a preferred embodiment of the invention, said therapeutic compound also comprises:
an agent that inhibits the activity of at least one gene selected from the group consisting of E2F1, EGR2, GLI1, JUN, MYC, SMAD3, SMAD4, SOX9, SRF, preferentially EGR2, SOX9
an agent that enhances the activity of at least one gene selected from the group consisting of ETS1, PPARG
for use in the prevention and/or treatment of fibrosis, hypertrophic scars or keloids.

Indeed, the inventors have found that these genes were involved in the fibrosis process and that their down-regulation or up-regulation would be useful for the treatment of fibrosis, hypertrophic scars or keloids.

Thus, the invention involves a novel gene therapy approach and/or a novel protein therapy approach.

As used herein, the expression "agent that inhibits the activity of a gene" or "inhibitor" refers to an agent than can downregulate said gene. It encompasses agents that act at the level of the gene expression, as well as agents that act at the level of the protein, either by decreasing the amount of protein present in a given cell, or by inhibiting the protein's activity.

As used herein, the expression "agent that enhances the activity of a gene" or "enhancer" refers to an agent than can upregulate said gene. It encompasses agents that act at the level of the gene expression, as well as agents that act at the level of the protein, either by increasing the amount of protein present in a given cell, or by increasing the protein's activity. It also encompasses agents that act upstream or downstream of said gene or protein in a signaling pathway.

In one embodiment the novel therapeutic comprises an inhibitor or enhancer of the gene expression, this inhibitor or enhancer can be either an anti-sense DNA or RNA, siRNA, shRNA, cDNA, TALENS or ribozymes, either naked or in the form of plasmid and viral vectors or a drug.

In a preferred embodiment, said therapeutic compound is a siRNA selected from the group consisting of siRNA having the sequence as set forth in SEQ ID No:11 to SEQ ID No:74 and mixtures thereof:

| Target gene | Sequence (5' → 3') | SEQ ID No: |
|---|---|---|
| CREB5 | CCGGCGAAGGGUGGUAGACGA | 11 |
|  | AACAGUAUUCUGUAGGAUCUA | 12 |
| E2F1 | UCGGAGAACUUUCAGAUCU | 13 |
|  | GAGAAGUCACGCUAUGAGA | 14 |
|  | GAGCAGAUGGUUAUGGUGA | 15 |
|  | GAACAGGGCCACUGACUCU | 16 |
| EGR2 | GAAGGCAUAAUCAAUAUUG | 17 |
|  | CUACUGUGGCCGAAAGUUU | 18 |
|  | GAAACCAGACCUUCACUUA | 19 |
|  | GAGAAGAGGUCGUUGGAUC | 20 |
| FOXS1 | AGGGCCAAUAAAGCCAUGUGA | 21 |
|  | CUGGCUCUAGGACCUGAAGAA | 22 |
| GLI1 | GCAAAUAGGGCUUCACAUA | 23 |
|  | AGGCUCAGCUUGUGUGUAA | 24 |
|  | GGACGAGGGACCUUGCAUU | 25 |
|  | CAGCUAGAGUCCAGAGGUU | 26 |
| HIC1 | GCACAGCAACGCAACCUCA | 27 |
|  | GAGCUUCCGUGACAACCUG | 28 |
|  | UGAUCAUCGUGGUGCAGAA | 29 |
|  | GACCAUCGACCGUUUCUCU | 30 |
| IRF7 | GCACAAGGUGUACGCGCUC | 31 |
|  | CAACUUCCGCUGCGCACUG | 32 |
|  | GCGCGCAUCUUCAAGGCCU | 33 |
|  | CAGGCACGGACCAGACUGA | 34 |
| JUN | GAGCGGACCUUAUGGCUAC | 35 |
|  | GAACAGGUGGCACAGCUUA | 36 |
|  | GAAACGACCUUCUAUGACG | 37 |
|  | UGAAAGCUCAGAACUCGGA | 38 |
| MYC | ACGGAACUCUUGUGCGUAA | 39 |
|  | GAACACACAACGUCUUGGA | 40 |
|  | AACGUUAGCUUCACCAACA | 41 |
|  | CGAUGUUGUUUCUGUGGAA | 42 |
| SMAD3 | CAACAGGAAUGCAGCAGUG | 43 |
|  | GAGUUCGCCUUCAAUAUGA | 44 |
|  | GGACGCAGGUUCUCCAAAC | 45 |
|  | UUAGAGACAUCAAGUAUGG | 46 |
| SMAD4 | GCAAUUGAAAGUUUGGUAA | 47 |
|  | CCCACAACCUUUAGACUGA | 48 |
|  | GAAUCCAUAUCACUACGAA | 49 |
|  | GUACAGAGUUACUACUUAG | 50 |
| SOX9 | GGAACAACCCGUCUACACA | 51 |
|  | GAACAAGCCGCACGUCAAG | 52 |
|  | GACCUUCCAUGUCAACGAG | 53 |
|  | GGAAGUCGGUGAAGAACCG | 54 |
| SRF | UGAGACAGGCCAUGUGUAU | 55 |
|  | GGACUGUGCUGAAGAGUAC | 56 |
|  | GCACCAAGAGUGAAUGAUC | 57 |
|  | GCACCAGUGUCUGCUAGUG | 58 |
| STAT1 | GCACGAUGGGCUCAGCUUU | 59 |
|  | CUACGAACAUGACCCUAUC | 60 |
|  | GAACCUGACUUCCAUGCGG | 61 |
|  | AGAAAGAGCUUGACAGUAA | 62 |
| STAT4 | GAACUAAACUAUCAGGUAA | 63 |
|  | GCAUGUAGCUGUGGUUAUU | 64 |
|  | CAAUCUAGCUACAGUGAUG | 65 |
|  | CUGCGAGACUACAAAGUUA | 66 |
| TCF4 | GCACUUCCUUCCAUCUAUU | 67 |
|  | GACAAAGAGCUGAGUGAUU | 68 |
|  | GCACAGCUGUUUGGUCUAG | 69 |
|  | CAACGGGACAGACAGUAUA | 70 |
| USF2 | GCAAGACGGGAGCGAGUAA | 71 |
|  | GGAGGGACAAGAUCAACAA | 72 |

-continued

| Target gene | Sequence (5' → 3') | SEQ ID No: |
|---|---|---|
| | GAAGAGCCCAGCACAACGA | 73 |
| | CAAAAUCCCUUCAGCAAUG | 74 |

These siRNA inhibit the expression of the target genes.

In one embodiment, the agent that enhances the activity of a gene is a cDNA.

Typically, the expression of the CREB5 gene can be enhanced by administering the CREB5 cDNA.

The same applies mutatis mutandis for all the other genes listed.

The cDNA can be administered or delivered to the fibrosis, hypertrophic scar or keloid to be treated in any suitable form known to the skilled person in art. It can be delivered as naked DNA, using plasmid vectors, viral vectors, or any other suitable means.

In another embodiment, the novel therapeutic comprises an inhibitor or enhancer of the protein encoded by the gene function, this inhibitor or enhancer can be either a binding agent that binds, either reversibly or irreversibly, to inhibit or enhance protein function such as an antibody or a known, or synthesized, protein agonist or antagonist; or an agent that works upstream or downstream of the protein signaling mechanism to inhibit or enhance the protein signaling and so negate or enhance the effects of expression of the protein in wound tissue.

Said agent (inhibitor or enhancer) can be any agent known in the art to act upon a given molecular target.

Typically, the enhancer of PPARG can be selected in the group consisting of thiazolidinediones, such as rosiglitazone and pioglitazone (Curr Drug Targets Cardiovasc Haematol Disord. 2005 October; 5(5):377-86. Role of PPAR-gamma agonist thiazolidinediones in treatment of pre-diabetic and diabetic individuals: a cardiovascular perspective. Dumasia R, Eagle K A, Kline-Rogers E, May N, Cho L, Mukherjee D).

Typically, the inhibitor of PPARG can be G3335 (CAS 36099-95-3) (Chembiochem. 2006 January; 7(1):74-82. The dipeptide H-Trp-Glu-OH shows highly antagonistic activity against PPARgamma: bioassay with molecular modeling simulation. Ye F, Zhang Z S, Luo H B, Shen J H, Chen K X, Shen X, Jiang H L.).

The therapeutic of the invention is for use in the treatment or prevention of fibrosis, hypertrophic scar or keloid. These fibrosis, hypertrophic scars or keloids are preferentially mammalian fibrosis, hypertrophic scars or keloids, more preferentially human fibrosis, hypertrophic scars or keloids.

An antibody for use in the invention is most ideally a monoclonal antibody or a humanized antibody.

In the above aspects and embodiments of the invention the therapeutic is formulated for topical application, but it can also be formulated for oral, cutaneous, transcutaneous, transdermal, intravenous or any application known.

Alternatively, in the above aspects of the invention the therapeutic is formulated for application into a dressing or impregnation of a dressing.

The therapeutic of the invention may be administered with an active agent. Such active agent may be an antibiotic or antibacterial agent, an antiseptic, an antiviral, an antifungal, an analgesic, an anti-inflammatory agent, a wound healing agent, a keratolytic agent, an anesthetic agent. Such actives are well known to skilled practitioners.

In another aspect of the invention, there is provided a pharmaceutical composition for use in treating fibrosis, hypertrophic scar or keloid comprising a therapeutic of the invention together with a pharmaceutical acceptable carrier.

Other active materials may also be present in the pharmaceutical composition, as may be considered appropriate or advisable for the fibrosis, hypertrophic scar or keloid or tissue susceptible of developing fibrosis, hypertrophic scar or keloid being treated.

The carrier, or, if more than one be present, each of the carriers, must be acceptable in the sense of being compatible with the other ingredients of the formulation and not deleterious to the recipient.

The formulations include those suitable for topical, oral, rectal, nasal or any administration known and may be prepared by any methods well known in the art of pharmacy.

The composition may be prepared by bringing into association the therapeutic of the invention and the carrier. In general, the formulations are prepared by uniformly and intimately bringing into association the active agent with liquid carriers or finely bringing into association the active with liquid carriers or finely divided solid carriers or both, and then if necessary shaping the product. The invention extends to methods for preparing a pharmaceutical composition comprising bringing a therapeutic of the invention in conjugation or association with a pharmaceutically acceptable carrier or vehicle.

For topical application to the skin, compounds of conventional use may be made up into a cream, ointment, gel, jelly, solution or suspension etc. Cream or ointment formulations that may be used for the composition are conventional formulations well known in the art.

Formulations for oral administration in the present invention may be presented as: capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

Additionally, or alternatively, the further aspect of the invention also, or alternatively, comprises a novel method for preventing and/or treating fibrosis, hypertrophic scar or keloid which method comprises:

administering to said fibrosis, hypertrophic scar or keloid:
an agent that inhibits the activity of at least one gene selected in the group consisting of HIC1, FOXS1, CREB5, IRF7, POU2F2, STAT4, TCF4 preferentially TCF4, FOXS1, STAT4
and/or
an agent that enhances the activity of at least one gene selected from the group consisting of MAF, MEOX2 and SIX2.

The invention also comprises a novel method for preventing and/or treating fibrosis, hypertrophic scar or keloid which method further comprises administering to said fibrosis, hypertrophic scar or keloid:
an agent that inhibits the activity of at least one gene selected from E2F1, EGR2, GLI1, JUN, MYC, SMAD3, SMAD4, SOX9 and SRF preferentially EGR2, SOX9
and/or
an agent that enhances the activity of at least one gene selected from ETS1, PPARG.

According to yet a further aspect of the invention there is provided a kit for preventing and/or treating fibrosis, hypertrophic scars or keloids which method comprises, wherein said kit comprises:
(a) at least one therapeutic as above described; and
(b) at least one medical device for applying to said fibrosis, hypertrophic scar or keloid or tissue susceptible of developing fibrosis, hypertrophic scar or keloid.

The term "medical device" includes an instrument, apparatus, implant, in vitro reagent, or similar or related article that is used to diagnose, prevent, or treat disease or other conditions, and does not achieve its purposes through chemical action within or on the body (which would make it a drug). Whereas medicinal products (also called pharmaceuticals) achieve their principal action by pharmacological, metabolic or immunological means, medical devices act by other means like physical, mechanical, or thermal means.

According to a yet further aspect of the invention there is provided a combination therapeutic for preventing and/or treating fibrosis, hypertrophic scars or keloids comprising an inhibitor or enhancer of gene expression and an inhibitor or enhancer of protein activity.

According to a further aspect of the invention there is provided a therapeutic for preventing and/or treating fibrosis, hypertrophic scars or keloids an inhibitor or enhancer of protein, or a homologue thereof.

According to a further aspect of the invention there is provided use of an inhibitor or enhancer of protein, or a homologue thereof, in the manufacture of a medicament for treating a fibrosis, hypertrophic scar or keloid or tissue susceptible of developing fibrosis, hypertrophic scar or keloid. According to a further aspect of the invention there is provided use of an inhibitor or enhance of protein, or a homologue thereof, for treating a fibrosis, hypertrophic scar or keloid or tissue susceptible of developing fibrosis, hypertrophic scar or keloid. The term "homologue" as used herein refers to amino acid sequences which have a sequence at least 50% homologous to the amino acid sequence of FOXS1, CREB5, E2F1, EGR2, ETS1, GLI1, HIC1, IRF7, JUN, MAF, MEOX2, MYC, POU2F2, PPARG, SIX2, SMAD3, SMAD4, SOX9, SRF, STAT4, TCF4 and which retain the biological activity of the FOXS1, CREB5, E2F1, EGR2, ETS1, GLI1, HIC1, IRF7, JUN, MAF, MEOX2, MYC, POU2F2, PPARG, SIX2, SMAD3, SMAD4, SOX9, SRF, STAT4, TCF4 sequence. It is preferred that homologues are at least 75% homologous to the FOXS1, CREB5, E2F1, EGR2, ETS1, GLI1, HIC1, IRF7, JUN, MAF, MEOX2, MYC, POU2F2, PPARG, SIX2, SMAD3, SMAD4, SOX9, SRF, STAT4, TCF4 peptide sequence and, in increasing order of preference, at least 80%, 85%, 90%, 95% or 99% homologous to the FOXS1, CREB5, E2F1, EGR2, ETS1, GLI1, HIC1, IRF7, JUN, MAF, MEOX2, MYC, POU2F2, PPARG, SIX2, SMAD3, SMAD4, SOX9, SRF, STAT4, TCF4 peptide sequence.

Treatment of fibrosis, hypertrophic scar or keloid described herein includes reference to human or veterinary use.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The full identity of the genes according to the invention is available on the NCBI database, or is well known to those skilled in the art.

The present invention will now be described by way of the following examples with particular reference to Figures and Table wherein:

FIGURE LEGENDS

FIGS. 1A-1B: Key transcription factors in fibroblast to myofibroblast differentiation.

FIG. 1A: Graphical explanation of the in silico gene network analysis;

FIG. 1B: Table representing the different transcription factors identified by bioinformatical and network analysis.

Figure 2A:
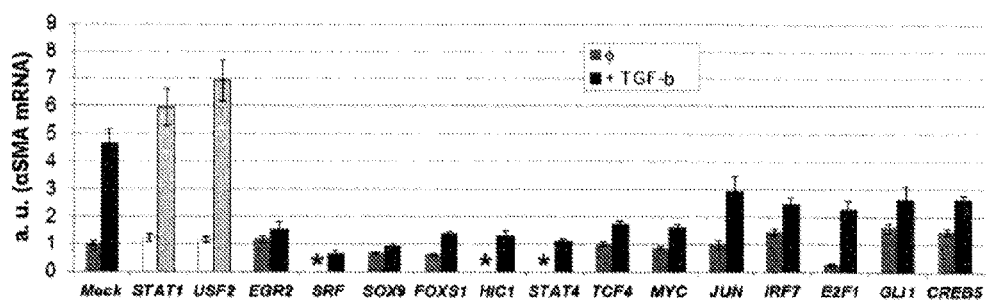

FIG. 2A: Graphic representation of the αSMA mRNA levels as assessed by RT-qPCR. NHDFs were treated either with mock siRNA or siRNA directed against different mRNA (FOXS1, EGR2, SRF, SOX9, HIC1, STAT4, TCF4, MYC, JUN, IRF7, E2F1, GLI1, CREB5 STAT1) and concomitantly subjected or not to TGFβ1 treatment. The RTqPCR were normalized with TUBB and the mock siRNA treated (TGF-b) condition was set to one. The treatments of NHDFs with siRNA against SRF, HIC1 or STAT4 lead to extensive cell death (*): no analysis was possible. The treatments of NHDFs with siRNA against STAT1 and USF2 represent a control experiment as these factors do not have any action on fibroblast to myofibroblast differentiation.

Figure 2B:
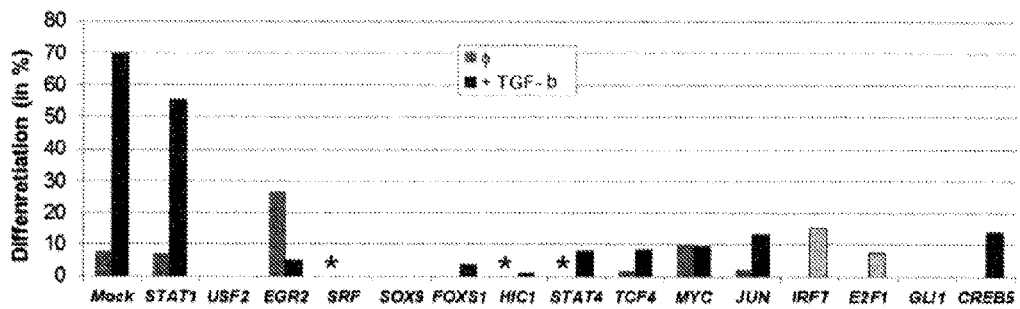

FIG. 2B: Graphic representation of the percentage of differentiated cells as assessed by the percentage of alpha SMA positive cells after treatment of NHDFs as described in FIG. 2A. The treatments of NHDFs with siRNA against SRF, HIC1 or STAT4 lead to extensive cell death (*): no analysis was possible. The treatments of NHDFs with siRNA against STAT1 and USF2 represent a control experiment as these factors do not have any action on fibroblast to myofibroblast differentiation.

Figure 2C:
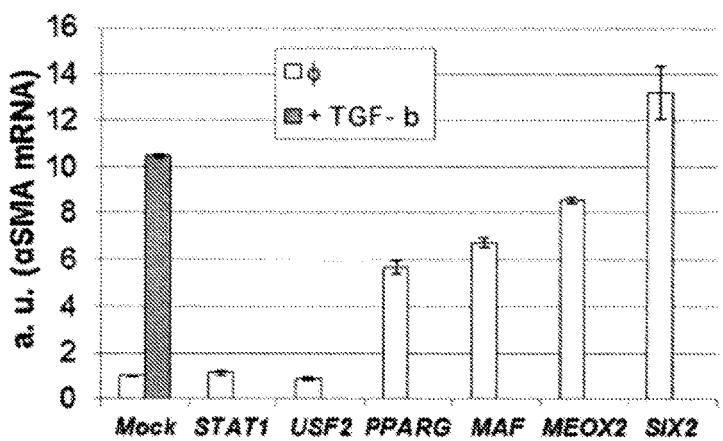

FIG. 2C: Graphic representation of the αSMA mRNA levels as assessed by RT-qPCR. Primary human dermal fibroblasts were treated either with mock siRNA or siRNA directed against different mRNA (PPARG, MAF, MEOX2, SIX2, STAT1 or USF2). The RTqPCR were normalized with TUBB and the mock siRNA treated (TGF-b) condition was set to 1. The treatments of NHDFs with siRNA against STAT1 and USF2 represent a control experiment as these factors do not have any action on fibroblast to myofibroblast differentiation.

Figure 3A:
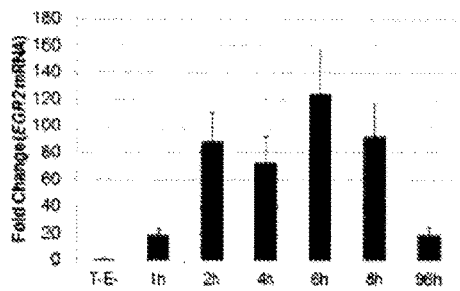
Figure 3A:
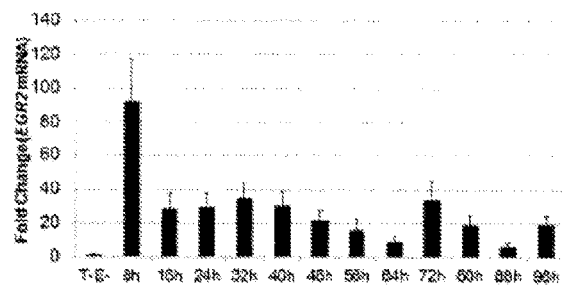
Figure 3B:
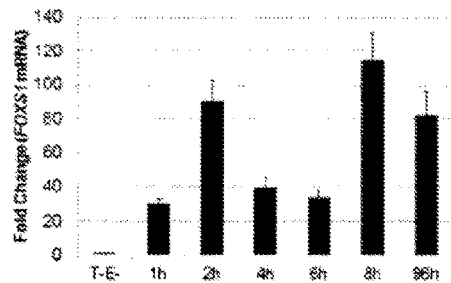
Figure 3B:
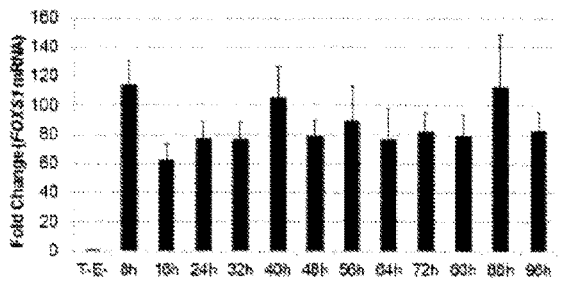
Figure 3C:
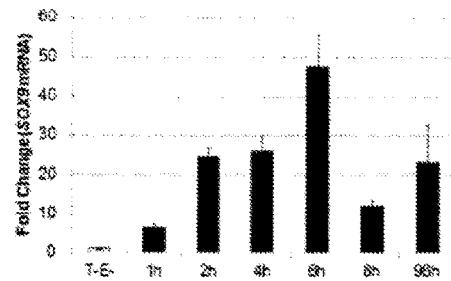
Figure 3C:
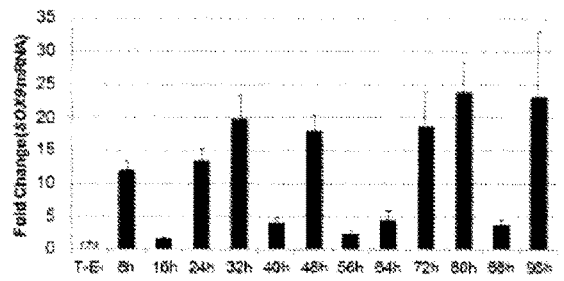
Figure 3D:
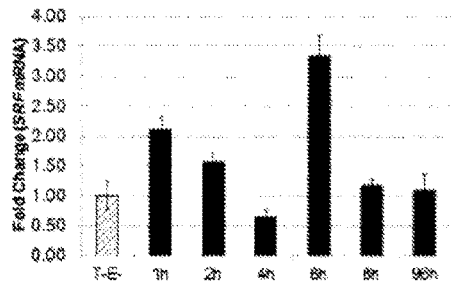
Figure 3D:
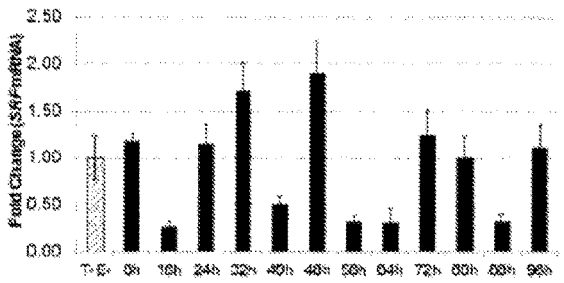
Figure 3E:
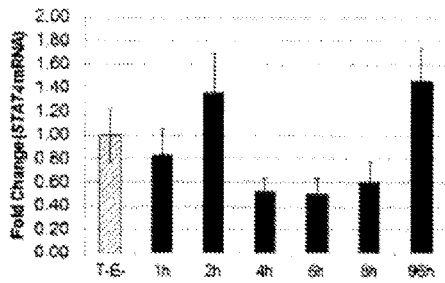
Figure 3E:
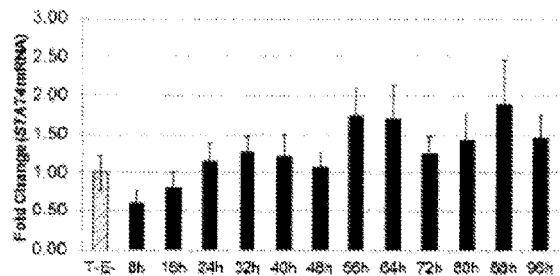
Figure 3F:
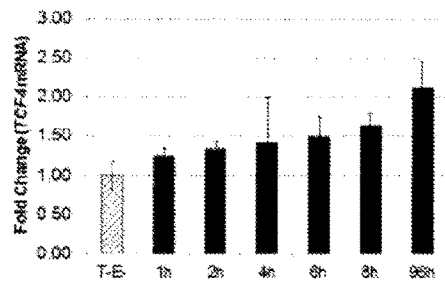
Figure 3F:
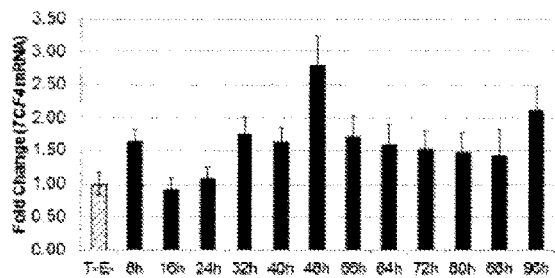
Figure 3G:
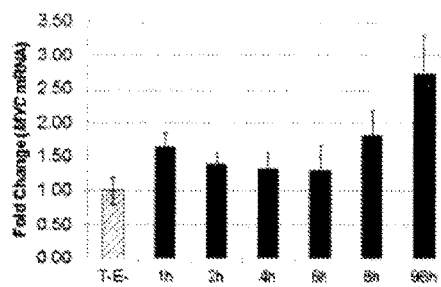
Figure 3G:
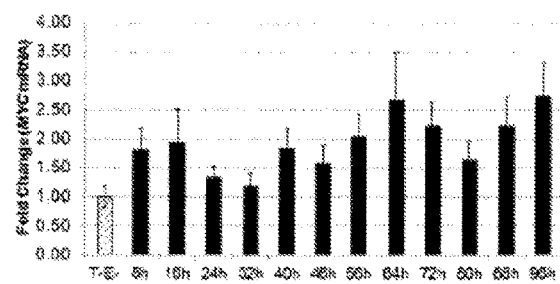
Figure 3H:
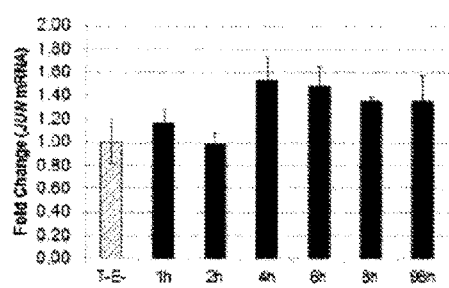
Figure 3H:
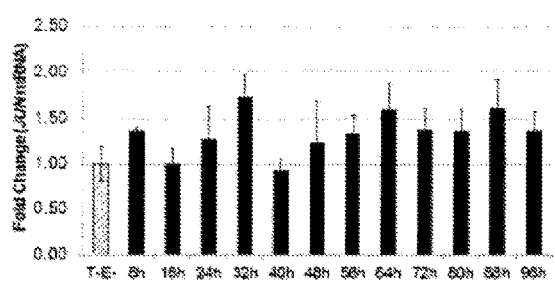
Figure 3I:
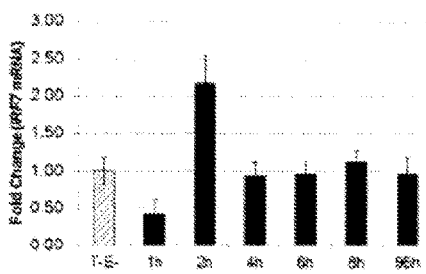
Figure 3I:
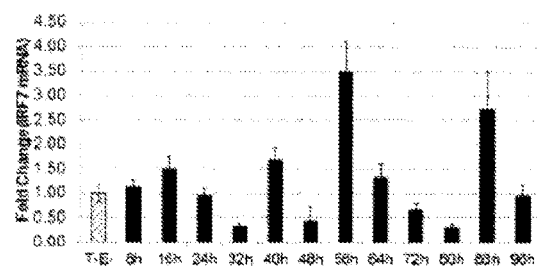
Figure 3J:
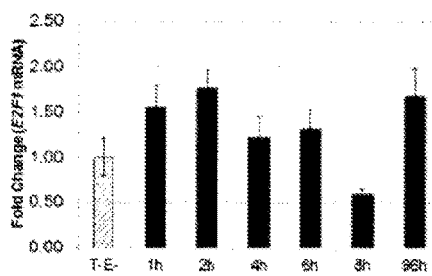
Figure 3J:
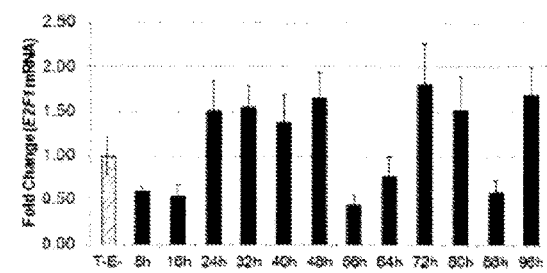
Figure 3K:
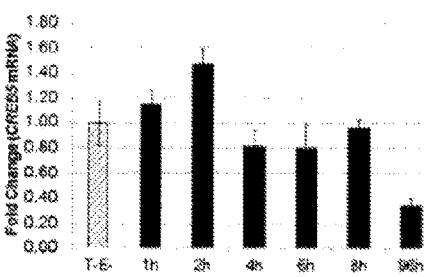
Figure 3K:
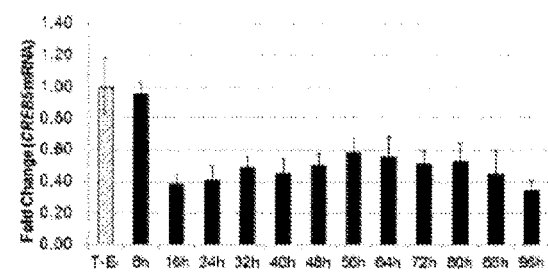
Figure 3L:
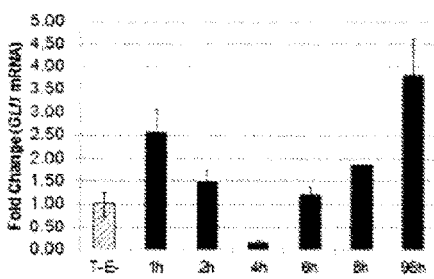
Figure 3L:
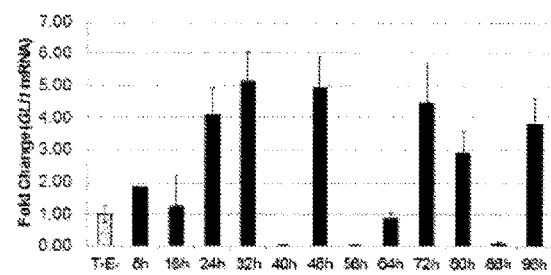
Figure 4A:
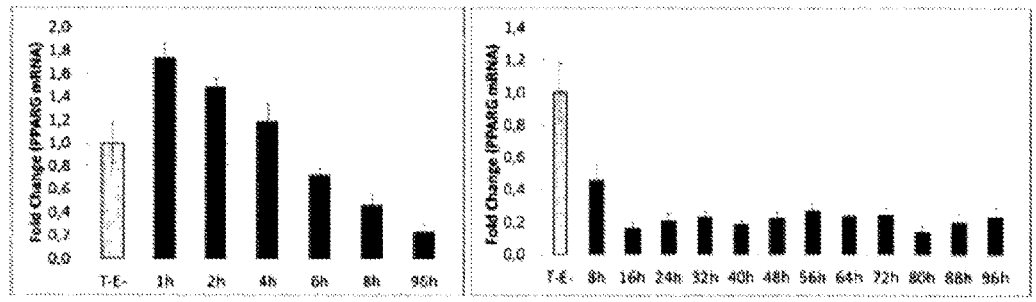
Figure 4B:
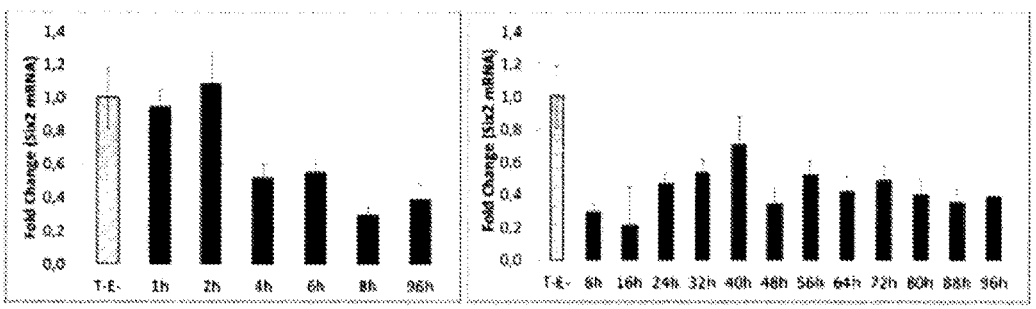
Figure 4C:
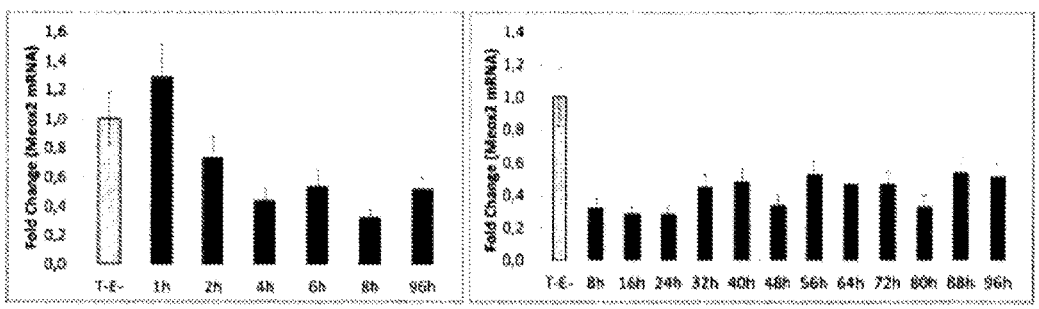
Figure 4D:
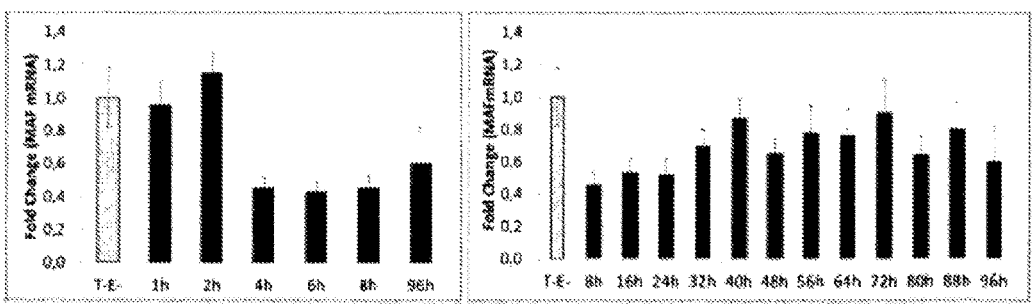
Figure 5A:
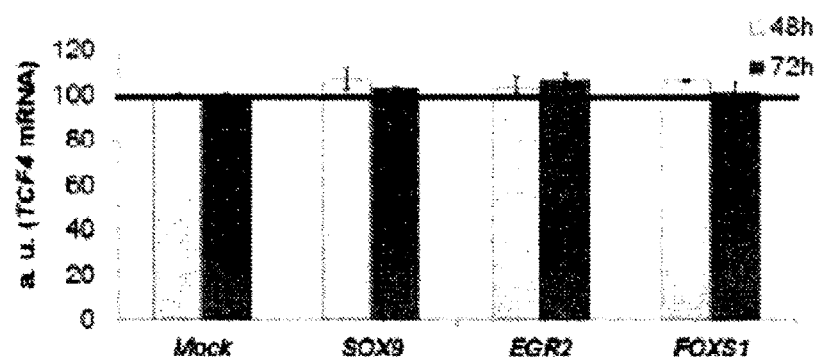
Figure 5B:
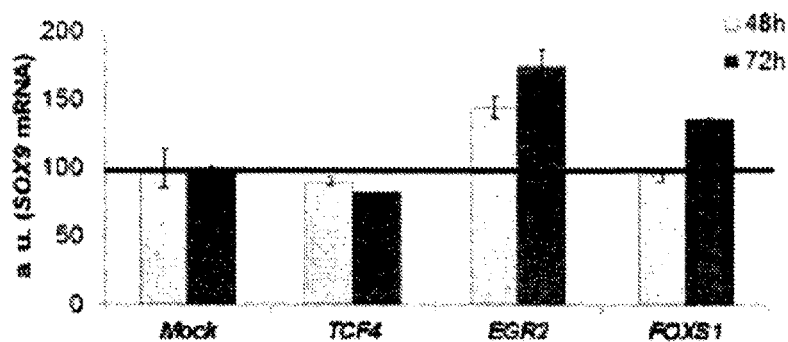
Figure 5C:
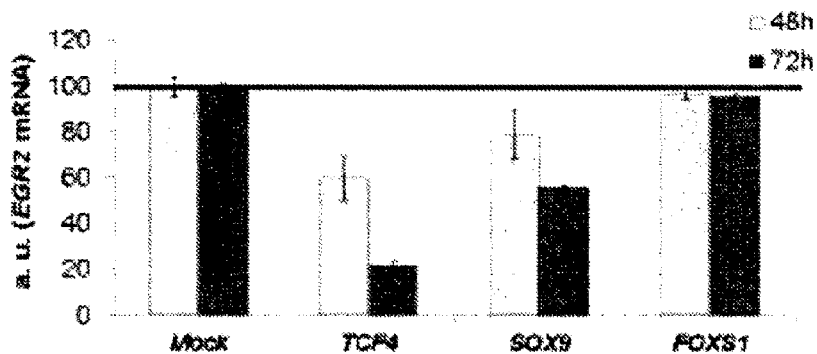
Figure 5D:
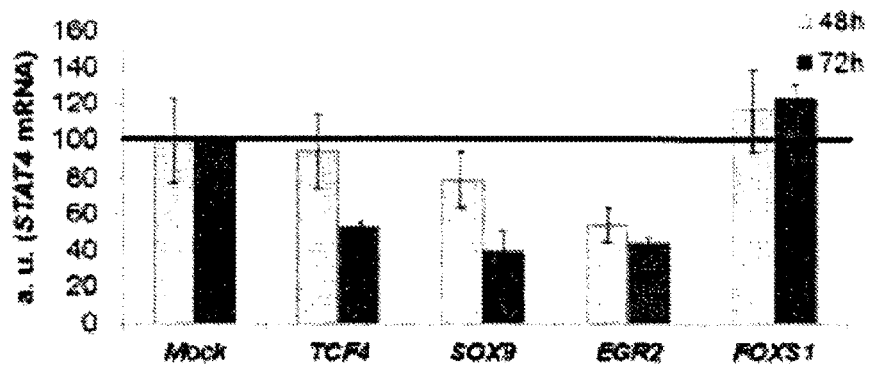
Figure 5E:
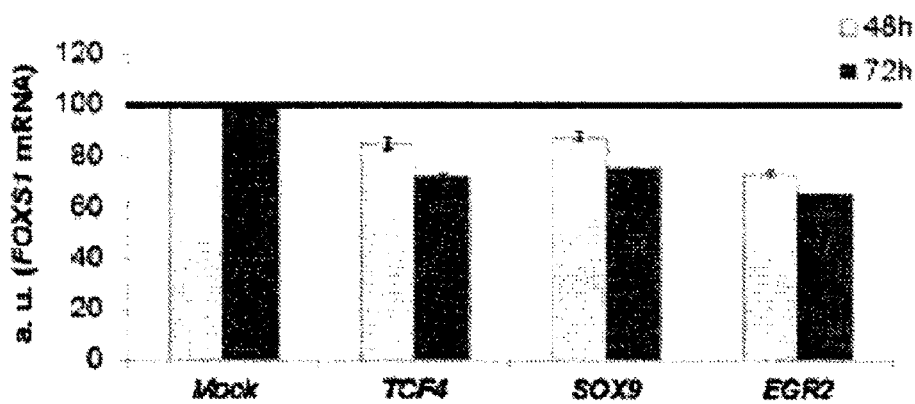
Figure 5F:
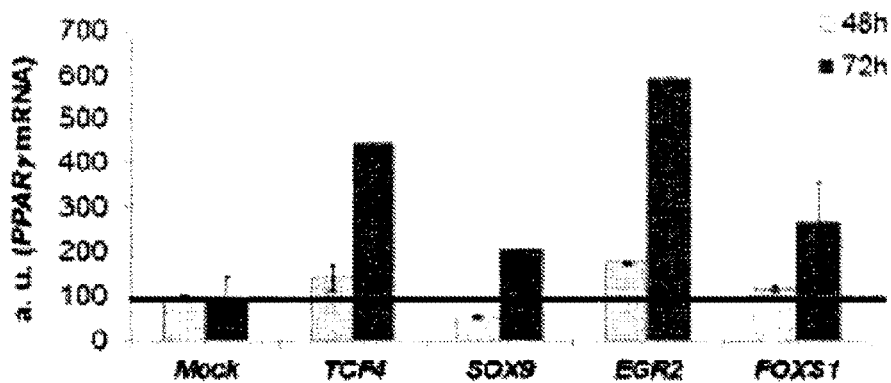
Figure 5G:
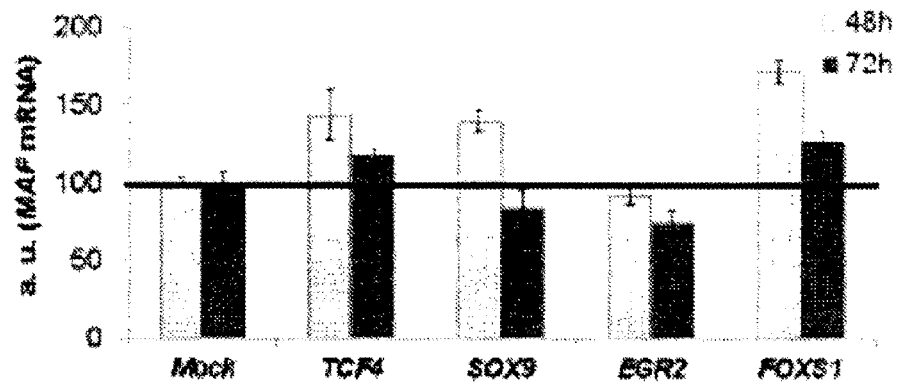
Figure 5H:
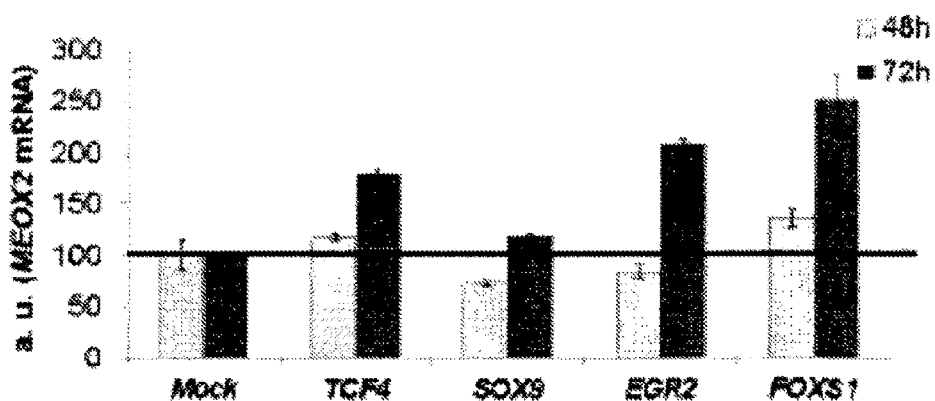
Figure 5I:
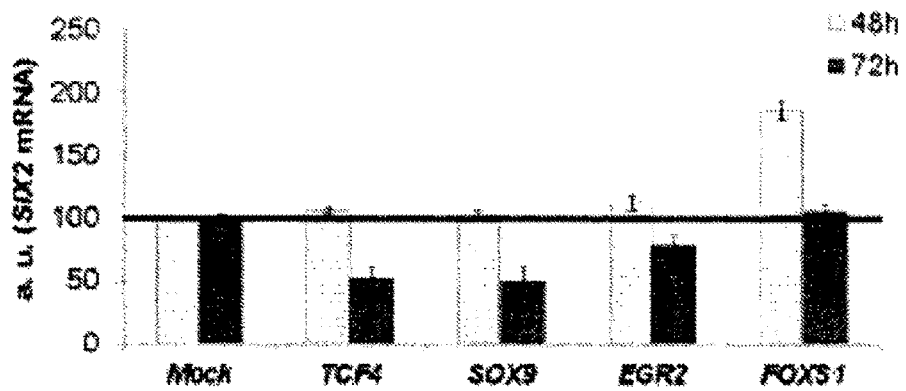

FIGS. 3A-3L: short and long timing after TGFβ1 treatment of FOXS1 (FIG. 3B), EGR2 (FIG. 3A), SRF (FIG. 3D), SOX9(FIG. 3C), HIC1(not depicted), STAT4(FIG. 3E), TCF4(FIG. 3F), MYC (FIG. 3G), JUN (FIG. 3H), IRF7 (FIG. 3I), E2F1(FIG. 3J), GLI1(FIG. 3L), CREB5(FIG. 3K). For each Factor, graphic representation of the mRNA levels after increasing time of treatment of the NHDF with TGFβ3 as assessed by RT-qPCR.

FIGS. 4A-4D: short and long timing after TGFβ1 treatment of PPARG (FIG. 4A), SIX2(FIG. 4B), MEOX2(FIG. 4C), MAF (FIG. 3C). For each Factor, graphic representation of the mRNA levels after increasing time of treatment of the NHDF with TGFβ as assessed by RT-qPCR.

FIGS. 5A-5I Graphic representation of the TCF4 (FIG. 5A), EGR2 (FIG. 5B), SOX9 (FIG. 5C), STAT4 (FIG. 5D), FOXS1 (FIG. 5E), PPARG (FIG. 5F), MAF (FIG. 5G), MEOX2 (FIG. 5H), and SIX2 (FIG. 5I) mRNA levels after NHDF (donor A) treatment for 48 h (light grey) or 72 h (dark grey) either with mock siRNA or siRNA directed against different TF mRNA (SOX9, EGR2, TCF4, or FOXS1) and concomitantly treated with TGF-β. For all graphs, the mock siRNA treated with TGF-β (T+E) condition was set to 100% for each time of treatment (48 h and 72 h).

FIG. 6 provides Table 1: identifying genes to increase or decrease to treat and/or prevent fibrosis, hypertrophic scars or keloids.

FIGS. 7A-7B provides Table 2: siRNA sequences against the target genes.

EXAMPLE

In response to a lesion, fibroblasts migrate into the wound where they differentiate into contractile myofibroblasts that will finally enter into apoptosis during the remodeling phase. This differentiation process can be studied ex-vivo in environmentally controlled tissue culture conditions, and therefore the timely controlled succession of different gene expression patterns can be addressed.

Materials and Methods

Establishment of an ex vivo Model of Fibrosis, Hypertrophic Scar or Keloid

Myofibroblasts represent the key players in the physiological reconstruction of skin after injury and in generating the pathological tissue deformations that characterize fibrosis such as hypertrophic scars (Desmouliere A, Chaponnier C, Gabbiani G (2005) Tissue repair, contraction, and the myofibroblast. Wound Repair Regen 13: 7-12).

To study the myofibroblasts involved in generating fibrosis, hypertrophic or keloid scars, NHDF were cultivated on collagen coated culture plates in DMEM-F12 (Invitrogen), supplemented with 10% FCS (Invitrogen), 5 Ng/mL of insulin and 1 ng/mL of b-FGF (PromoKine) and 10 ng/mL of TGF-O1 (Promocell), as TGF-O1 is known to induce the expression of αSMA in fibroblasts (Desmouliere A, Geinoz A, Gabbiani F, Gabbiani G 13 (1993) Transforming growth factor-beta 1 induces alpha-smooth muscle actin expression in granulation tissue myofibroblasts and in quiescent and growing cultured fibroblasts. J Cell Biol, 1993 July, 122(1): 103-111).

The efficiency of fibroblast differentiation was estimated by analyzing the expression of the myofibroblast marker alpha smooth muscle actin (αSMA).

This αSMA expression was assessed by RT-qPCR (mRNA levels) and by Western Blot (protein).

The efficiency of fibroblast differentiation was estimated by analyzing the expression of the myofibroblast marker alpha smooth muscle actin (αSMA).

Western Blotting Assay

Total proteins were extracted by scratching the cells with lysis buffer (TRIS, NaCl, NP40, EDTA, IMDTT) and incubated 30 min in ice. To remove cell debris, the samples were centrifuged at 13,000×g for 10 min at 4° C. and store at −20° C. until use. Protein concentration was determined according to BCA method (Sigma). Equal amounts of total protein (20 μg) were loaded to NuPAGE 10% BIS-Tris gel (Invitrogen), separated by migration at 150 V, and transferred to nitrocellulose membrane (Whatman) 1 hour at 30 V. Then, membranes were stained for αSMA (Abcam) and tubulin (Abcam). Incubations were followed by secondary antibodies goat anti-rabbit IgG and goat anti-mouse IgG, respectively, conjugated with horseradish-peroxidase (HRP) (Promega). Signals were detected by ECL chemiluminescence using UptiLight HS WB Substrate (Uptima, Interchim). Bands were digitized with a scanner and the ratio between all bands density of the same blot was calculated by software (ImageJ 1.43 u, 64-bit). Relative αSMA expression was normalized to the respective value for tubulin.

Total RNA Sample Preparation

After four days of experiment, treated fibroblasts were lysed with TRIzol Reagent (Invitrogen) and stored at −80° C. Then RNA was purified using chloroform and precipitated by isopropanol. Total RNA was quantified on the NanoDrop 2000c Spectrophotometer (Thermo Scientific). Reverse transcription of 500 ng total RNA to cDNA was done with oligot dT (Invitrogen) using SuperScript III RT (Invitrogen) and RNAse OUT (Invitrogen). The cDNA was store at −20° C.

Quantitative Real-Time RT-PCR

Quantitative real-time PCR (RT-qPCR) was done using 5 μL of 1:20 diluted cDNA on the LightCycler480 system (Roche) using Maxima SYBR Green qPCR Master Mix (Fermentas). Forward and reverse primers were designed by Eurofins (MWG, αSMA forward: CTGTTTTCCCATCCATTGTG (SEQ ID NO:9), αSMA reverse: CCATGTTCTATCGGGTACTT (SEQ ID NO:10)) and a 100 μM stock was stored at −20° C. Forward and reverse primer pairs were used for each RT-qPCR reaction. The cycling conditions were as follows: an initial 95° C. for 10 minutes, followed by 45 cycles of 95° C. for 15 sec, 58° C. for 30 sec, 72° C. for 20 sec. LightCycler 480 SW 1.5 was used to evaluate the TM curves, to determine the Cp and to approximate the relative concentration for each amplification reaction.

siRNA Treatment

The expression the different TF was knocked down by transiently transfecting NHDF with specific small interfering RNAs. At least two different siRNAs (Qiagen) or highly specific ON TARGET PLUS smartpool siRNAs (Thermo Scientific) were used for each target. NHDF were treated with 10 nM siRNA and 4 μL of INTERFERin reagent (PolyPlus, Ozyme), according to the manufacturer's instruction and concomittanty treated with TGF-β1 and exudates for 6 days. To maintain a sufficient knocking down, a second transfection was performed at 48 h after the first one. The efficiency of the knock down was assessed 48 h after the first transfection.

α-Smooth Muscle Actin Immunofluorescence

Cells grown in collagen coated culture dishes, and treated as previously described, were fixed with 4% paraformaldehyde (PFA) in PBS for 15 minutes and permeabilized with 2.5% Triton X-100 (Euromedex, 2000-B) in PBS for 3 minutes. After saturation with 5% BSA in PBS, cells were stained for α-SMA (Abcam, ab5694) and for DNA (DAPI). As secondary antibody, CyTM3 conjugated anti rabbit (GE Healthcare, PA43004) was used. Samples were observed with an oil immersion objective (Plan Fluor 40X/1.30 Oil, Nikon) on a Nikon ECLIPSE Ti (Nikon). Digital images were taken with a digital camera (Cool SNAP HQ$^2$, Photometrics) and software (MetaMorf 7.5.4.0). To estimate the percentage of fibroblast differentiation due to the different treatments, the total number of cells per field was determined by the DAPI, and myofibroblasts, differentiated fibroblasts, were counted using the α-SMA staining. Then, STUDENT (t-) and $\chi^2$ tests were realized to evaluate the differentially expression of αSMA between the untreated fibroblasts (without TGFβ) and the treated ones.

Network Analysis

In order to enlighten master regulators of fibroblast fate after each different treatment, we have performed a gene network analysis treating gene expression lists determined after mRNA seq deep sequencing analysis of the gene profile of fibroblasts treated with TGF β with the gene profile of fibroblast treated without TGFβ. In these analysis and based on the assumption that the decrease or increase of interconnected genes is of stronger significance than a significant Log FC, we have used lists of genes selected only based on their P value and not on the value of their Log FC. We have performed two types of analysis: an ingenuity "upstream regulator analysis" and a DIRE analysis. The Ingenuity "upstream regulator analysis", given the particular profile of genes expression between two conditions, consists in selecting potential upstream regulators. The DIRE analysis is based on the selection of potential common regulatory elements between genes based on these elements conservation during evolution. From these identified elements, DIRE is able to provide a list of master regulators for a list of co-regulated genes. From those two analyses, and for each list analyzed, we have selected Transcription Factors (TFs) expressed in at least one of the two conditions considered in the concerned list (i.e. number of sequencing his superior to twenty in at least one of the two conditions). Then, we have deeply compared the two sets of analysis and decided to keep in the "key regulators lists" transcription factors belonging to both analyses. Because of possible bias in these two analyses we also decided to rescue transcription factors belonging only to one analysis and not the other but presenting very interesting target genes pattern in one list or the other. Altogether, these genes networks analysis allowed us to propose a list of TFs being key regulators in one or the other fibroblast fate (FIG. 1)

Gene Expression Route upon Fibroblast to Myofibroblast Differentiation

Identification of the Main Molecular Targets Implicated in Fibroblast Differentiation of Human Primary Fibroblasts Under Normal and Pathological Conditions We have performed an in silico gene network analysis to enlighten putative upstream regulators of the different gene expression routes defined previously. This approach was original in the sense that we used global gene network analysis to identify potential key regulators and we did not take into account a change in these factors expression to select them. For example, we used the DIRE program to identify evolutionary conserved potential regulatory elements in the different genes lists which allowed us to enlighten transcription factors that could potentially bind to these elements and thus regulate these sets of genes. Twenty-three transcription factors were selected out from this analysis.

To prioritize the extensive study of the different Transcription Factors (TFs), we performed a time response study of TFs after the different fibroblast treatments. We did a short (between 30 mn and 8 hours) and a long (between 8 hours and 96 hours) analysis of their changes in expression after the different treatments (FIGS. 3 and 4).

We have performed an exhaustive siRNA-based approach to study in one hand the role of these different factors in normal fibroblast to myofibroblast differentiation pathway (FIG. 2).

The siRNA knock-down of fourteen of the potential key transcription factors identified therein inhibited the fibroblast to myofibroblast differentiation pathway as assessed by analyzing the αSMA expression from TGFβ and siRNA-treated NHDFs: GLI1, HIC1, TCF4, SOX9, STAT4 MYC, CREB5, IRF7, JUN, E2F1, EGR2, SRF, FOXS1 as their knockdown decreased inhibit more or less efficiently the myofibroblast differentiation (FIG. 2a-b-c). Very interestingly, except for SOX9, FOXS1 and EGR2 which expression is strongly and rapidly up regulated upon TGFβ treatment, the mRNA levels of the other factors is constant during the first day or so after TGFβ treatment and overall unchanged during the four days of differentiation. This indicates that the maintenance of their expression but not their over-expression is necessary for fibroblast to myofibroblast differentiation.

The siRNA knock-down of four other potential key transcription factors identified by the in silico analysis (MAF, SIX2, MEOX2 and PPARG) seemed to induce the fibroblast to myofibroblast differentiation in absence of TGFβ to the same extend as the one obtained with mock transfected cells treated with TGFβ. Altogether these results showed that with knocking-down approaches we were able either to reduce or induce fibroblast to myofibroblast differentiation (Table 1).

An in silico gene network analysis allowed us to identify potential key regulators of fibroblast cell fate either during differentiation into. By knocking down approaches, we found a strong effect on differentiation for nineteen of these factors.

We have also identified factors which seemed to play a role but maybe not as strongly as the ones described in the paragraph before as their knockdown leads to consistent but mild decrease of αSMA expression. These factors are MYC, JUN, E2F1, IRF7 and CREB5.

Very interestingly, we showed that the inactivation of some transcription factors leads to an increase of fibroblast differentiation per se. The knocking down of PPARG mRNA leads to an increase of fibroblast to myofibroblast differentiation.

FOXS1 belongs to the forkhead family of transcription factor often involved in developmental processes such as morphogenesis and differentiation. It has been shown that FOXS1 is of primary importance in the development of testicular vasculature. Moreover, FOXS1 was described as an early sensory neuronal marker. Here we show that inactivation of FOXS1 leads to an increase of myofibroblast differentiation in absence of TGFβ.

MEOX2 has already been described as implicated in TGFβ pathway as it was identified as an important factor in cleft palate development in TGFβ3 knockout mice. Experiments in C2C12 myoblast cells showed that MEOX2 is also important for skeletal muscle development and differentiation. Here, we showed that siRNA directed against MEOX2 lead to a bypass of the exudate effect by fibroblasts to be able to differentiate into myofibroblasts.

In T cells, it has been shown that MAF was responsible for inhibition of IL22 expression by neutralizing TGFβ. TGFβ and MAF have antagonist/opposite effects on IL21 expression in CD4(+) T cells. In the same connection, in this study, we implicated MAF as an inhibitor of fibroblast to myofibroblast differentiation in absence or presence of exudate as its inactivation by siRNA leads to an increase of myofibroblast differentiation. On the contrary, during chondrocyte differentiation, a long form of MAF interacts and cooperates with SOX9 to activate downstream targets. This is another example of the differences between myofibroblast and chondrocyte differentiations.

SIX2 has been involved in maintaining pluripotency in kidney: in embryonal renal mesenchyme cells it is able to suppress differentiation and during kidney development it maintains the progenitor pool. Here, in dermal fibroblast, the invalidation of SIX2 leads to a bypass of the dominant exudate effect on TGFβ signaling.

Regulatory Interactions Between Key Transcription Factors During Fibroblast to Myofibroblast Differentiation The expression of TCF4 mRNA was not modified after SOX9, EGR2 or FOXS1 knockdown (FIG. 5) placing it at the top of the regulatory interaction network between these factors. On the contrary EGR2 expression was largely inhibited upon siRNA treatment against TCF4 and SOX9 but remained unchanged upon treatment against FOXS1 (FIG. 5) placing it after TCF4 and SOX9 but before FOXS1 in the network. SOX9 mRNA remained largely unchanged upon TCF4 and FOXS1 knockdown. We placed FOXS1 as a downstream target of SOX9. On the contrary SOX9 is upregulated upon EGR2 knockdown (FIG. 5) The STAT4 mRNA is downregulated by TCF4, SOX9 and EGR2 knockdown (FIG. 5) placing is as a downstream target of those TF whereas it remained unchanged upon FOXS1 siRNA treatment placing it beforehand. Consistently, FOXS1 mRNA is downregulated upon TCF4, SOX9 and EGR2 siRNA treatment (FIG. 5) placing it at the end of this cascade. Globally, the PPARG, MAF and MEOX2 mRNA were upregulated upon siRNA treatment against TCF4, SOX9, EGR2 and FOXS1 (FIG. 5) consistent with their role as antagonist in fibroblast differentiation. SIX2 mRNA level was unchanged upon EGR2 and FOXS1 knockdown (FIG. 5) but upregulated in the same manner by TCF4 and SOX9 consistent with a close interconnection between these two TF and suggesting the existence of a balanced signal between the differentiation agonists SOX9 and TCF4 and the antagonist SIX2.

The identification of transcription factors able to bypass differentiation is of major importance in the fibrosis, hypertrophic scar or keloid. In this study, by focusing on fibroblast, by no mean we tried to dissimulate the importance of other cells like neutrophils and macrophages in the skin healing process but we willingly simplified the biological context to draw a clearer picture of the situation.

Cancer Connection

Myofibroblast are not only key cells in fibrosis, their importance has long been proven in cancer too where the presence of myofibroblast in the stroma as "cancer associated fibroblast" facilitate tumor development and has been often associated with inflammation, cell invasion, high grade malignancy and poor prognosis. Myofibroblast are enriched in stroma from prostate cancer compared to benign prostatic hyperplasia and associated at the leading edge of carcinomas. They produce MMP, cytokines (IL8, VEGF) and chemokines (CXCL12) to promote cancer proliferation, tumor invasion and neo-angiogenesis. As alternative therapeutic tracks, it seems of primary importance to target stromal cells (and among them myofibroblasts) in cancer to diminish its abilities to migrate, invade and proliferate. But the cancer case is not so trivial; it has been suggested that, as inflammation is often linked to cancer, finding new ways of bypassing or inhibiting inflammation could also help fighting against cancer. This extensive study on TGFβ-dependent fibroblast to myofibroblast differentiation gives a lot of new paths for therapeutic targets discovery. Nonetheless, because of TGFβ dual pro-fibrosis and anti-inflammation activities, therapeutics playing with inhibition or re-enforcement of TGFβ action should be well-balanced as inhibition of fibrosis via inhibition of TGFβ pathway could also increase cancer susceptibility.

The better understanding of normal fibroblast to myofibroblast differentiation is of major importance in the field as it opens new ways into novel therapeutics markers or targets that can be used in other important pathologies.

Tissue fibrosis (like pulmonary fibrosis, liver fibrosis, renal interstitial fibrosis, cardiovascular fibrosis, hypertrophic or keloid scars . . . ) is primarily attributed to an excessive activation of ECM producing myofibroblasts by TGFβ1. A better understanding of the gene expression route from fibroblast to myofibroblast is of great interest in the fibrosis understanding and curing. We showed that exudate from chronic wounds are able to prevent and reverse the myofibroblast differentiation giving new signs of the reversibility of differentiation as it has already been shown for liver, kidney or Hepato Stellar Cell (HSC) derived myofibroblast. We also identify transcription factors which inactivation inhibits TGFβ-dependent myofibroblast differentiation. Myofibroblasts are not only key cells in fibrosis, their importance has been long proven in cancer too where the presence of myofibroblast in the stroma as "cancer associated fibroblast" facilitate tumor development and has been often associated with inflammation, cell invasion, high grade malignancy and poor prognosis. Myofibroblast are enriched in stroma from prostate cancer compared to benign prostatic hyperplasia and associated at the leading edge of carcinomas. They produce MMP, cytokines (IL8, VEGF) and chemokines (CXCL12) to promote cancer proliferation, tumor invasion and neo-angiogenesis. As alternative therapeutic tracks, it seems of primary importance to target stromal cells (and among them myofibroblasts) in cancer to diminish its abilities to migrate, invade and proliferate. But the cancer case is not so trivial; it has been suggested that, as inflammation is often linked to cancer, finding new ways of bypassing or inhibiting inflammation could also help fighting against cancer. The study on TGFβ-dependent fibroblast to myofibroblast differentiation shows a lot of new paths for therapeutic targets discovery. Nonetheless, because of TGFβ dual pro-fibrosis and anti-inflammation activities, therapeutics playing with inhibition or re-enforcement of TGFβ action should be well-balanced as inhibition of fibrosis via inhibition of TGFβ pathway could also increase cancer susceptibility.

The invention claimed is:

1. A method for preventing and/or treating skin fibrosis, hypertrophic scar or keloid in a subject in need thereof, comprising administering to said skin fibrosis, hypertrophic scar, or keloid, or to tissue susceptible to developing skin fibrosis, hypertrophic scar, or keloid, a therapeutic compound comprising:
   an agent that inhibits the expression of FOXS1, and/or an agent that inhibits the expression TCF4, and/or an agent that enhances the expression of MAF.

2. The method according to claim 1 further comprising: administering to the skin fibrosis, keloid, hypertrophic scar or tissue susceptible to developing skin fibrosis, hypertrophic scar, or keloid an agent that inhibits expression of SOX9.

3. The method according to claim 1 wherein the agent that inhibits expression of FOXS1 and/or the agent that enhances expression of MAF are selected from the group consisting of antisense DNA, antisense RNA, siRNA, shRNA, and ribozymes directed to FOXS1 RNA, optionally in the form of a plasmid or viral vector.

4. The method according to claim 1 wherein the agent that inhibits the expression of TGF4 and/or the agent that enhances the expression of MAF are selected from the group consisting of: anti-sense DNA, anti-sense RNA, siRNA shRNA, and ribozymes directed to TCF4 RNA, optionally in the form of plasmid and viral vectors.

5. The method according to claim 1 wherein the agent that enhances the expression of MAF is a cDNA encoding MAF, optionally in the form of a plasmid or viral vector.

6. The method according to claim 1 wherein it is for treating mammalian skin fibrosis, hypertrophic scars, or keloid, or tissue susceptible to developing skin fibrosis, hypertrophic scar, or keloid.

7. The method according to claim 1 wherein it is for treating human skin fibrosis, hypertrophic scars, keloid, or tissue susceptible to developing skin fibrosis, hypertrophic scar, or keloid.

8. The method according to claim 1 wherein the therapeutic compound is for topical application.

9. The method according to claim 1 wherein the therapeutic compound is for application to a dressing or impregnation of a dressing.

10. The method according to claim 1 further comprising administering to said skin fibrosis, hypertrophic scar, keloid, or tissue susceptible to developing skin fibrosis, hypertrophic scar or keloid at least one further therapeutic.

11. A method for treating a mammalian skin fibrosis, hypertrophic scar, keloid, or tissue susceptible to developing skin fibrosis, hypertrophic scar, or keloid, wherein said method comprises administering to said skin fibrosis, hypertrophic scar, keloid, or tissue susceptible to developing skin fibrosis, hypertrophic scar, or keloid a therapeutic compound comprising:
   an agent that inhibits the expression of FOXS1, and/or an agent that inhibits the expression TCF4, and/or an agent that enhances the expression of MAF.

12. A method for treating a skin fibrosis, hypertrophic scar, keloid, or tissue susceptible to developing skin fibrosis, hypertrophic scar, or keloid, comprising administering to said skin fibrosis, hypertrophic scar, keloid, or skin tissue susceptible to developing fibrosis, hypertrophic scar, or keloid:
   an agent that inhibits the expression of FOXS1, and/or an agent that inhibits the expression TCF4, and/or an agent that enhances the expression of MAF, wherein said agent modulates fibroblast and myofibroblast differentiation and/or activity.

* * * * *

SEQUENCE LISTING

<160> NUMBER OF SEQ ID NOS: 74

<210> SEQ ID NO 1
<211> LENGTH: 21
<212> TYPE: RNA
<213> ORGANISM: Artificial Sequence
<220> FEATURE:
<223> OTHER INFORMATION: siRNA

<400> SEQUENCE: 1
uucgaucuga ugaaguuuga a                                              21

<210> SEQ ID NO 2
<211> LENGTH: 21
<212> TYPE: RNA
<213> ORGANISM: artificial
<220> FEATURE:
<223> OTHER INFORMATION: siRNA

<400> SEQUENCE: 2
cggcaggaga auggcaucag a                                              21

<210> SEQ ID NO 3
<211> LENGTH: 21
<212> TYPE: RNA
<213> ORGANISM: artificial
<220> FEATURE:
<223> OTHER INFORMATION: siRNA

<400> SEQUENCE: 3
agcaugcgca cuuaugauau a                                              21

<210> SEQ ID NO 4
<211> LENGTH: 21
<212> TYPE: RNA
<213> ORGANISM: artificial
<220> FEATURE:
<223> OTHER INFORMATION: siRNA

<400> SEQUENCE: 4
cccgcccguc cugugcucca a                                              21

<210> SEQ ID NO 5
<211> LENGTH: 21
<212> TYPE: RNA
<213> ORGANISM: artificial
<220> FEATURE:
<223> OTHER INFORMATION: siRNA

<400> SEQUENCE: 5
uccggagaac aaucagauug a                                              21

<210> SEQ ID NO 6
<211> LENGTH: 21
<212> TYPE: RNA
<213> ORGANISM: artificial
<220> FEATURE:
<223> OTHER INFORMATION: siRNA

<400> SEQUENCE: 6
gagggcgauc uugacaggaa a                                              21

<210> SEQ ID NO 7
<211> LENGTH: 21
<212> TYPE: RNA
<213> ORGANISM: artificial

```
<220> FEATURE:
<223> OTHER INFORMATION: siRNA

<400> SEQUENCE: 7
caacgagaac uccaauucua a                                              21

<210> SEQ ID NO 8
<211> LENGTH: 21
<212> TYPE: RNA
<213> ORGANISM: artificial
<220> FEATURE:
<223> OTHER INFORMATION: siRNA

<400> SEQUENCE: 8
cccgcugaau ggcagcggca a                                              21

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
ctgttttccc atccattgtg                                                20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
ccatgttcta tcgggtactt                                                20

<210> SEQ ID NO 11
<211> LENGTH: 21
<212> TYPE: RNA
<213> ORGANISM: artificial
<220> FEATURE:
<223> OTHER INFORMATION: siRNA

<400> SEQUENCE: 11
ccggcgaagg gugguagacg a                                              21

<210> SEQ ID NO 12
<211> LENGTH: 21
<212> TYPE: RNA
<213> ORGANISM: artificial
<220> FEATURE:
<223> OTHER INFORMATION: siRNA

<400> SEQUENCE: 12
aacaguauuc uguaggaucu a                                              21

<210> SEQ ID NO 13
<211> LENGTH: 19
<212> TYPE: RNA
<213> ORGANISM: artificial
<220> FEATURE:
<223> OTHER INFORMATION: siRNA

<400> SEQUENCE: 13
ucggagaacu uucagaucu                                                 19
```

```
<210> SEQ ID NO 14
<211> LENGTH: 19
<212> TYPE: RNA
<213> ORGANISM: artificial
<220> FEATURE:
<223> OTHER INFORMATION: siRNA

<400> SEQUENCE: 14
gagaagucac gcuaugaga                                                  19

<210> SEQ ID NO 15
<211> LENGTH: 19
<212> TYPE: RNA
<213> ORGANISM: artificial
<220> FEATURE:
<223> OTHER INFORMATION: siRNA

<400> SEQUENCE: 15
gagcagaugg uuaugguga                                                  19

<210> SEQ ID NO 16
<211> LENGTH: 19
<212> TYPE: RNA
<213> ORGANISM: artificial
<220> FEATURE:
<223> OTHER INFORMATION: siRNA

<400> SEQUENCE: 16
gaacagggcc acugacucu                                                  19

<210> SEQ ID NO 17
<211> LENGTH: 19
<212> TYPE: RNA
<213> ORGANISM: artificial
<220> FEATURE:
<223> OTHER INFORMATION: siRNA

<400> SEQUENCE: 17
gaaggcauaa ucaauauug                                                  19

<210> SEQ ID NO 18
<211> LENGTH: 19
<212> TYPE: RNA
<213> ORGANISM: artificial
<220> FEATURE:
<223> OTHER INFORMATION: siRNA

<400> SEQUENCE: 18
cuacuguggc cgaaaguuu                                                  19

<210> SEQ ID NO 19
<211> LENGTH: 19
<212> TYPE: RNA
<213> ORGANISM: artificial
<220> FEATURE:
<223> OTHER INFORMATION: siRNA

<400> SEQUENCE: 19
gaaaccagac cuucacuua                                                  19

<210> SEQ ID NO 20
<211> LENGTH: 19
<212> TYPE: RNA
<213> ORGANISM: artificial
<220> FEATURE:
<223> OTHER INFORMATION: siRNA
```

<400> SEQUENCE: 20
gagaagaggu cguuggauc                                                19

<210> SEQ ID NO 21
<211> LENGTH: 21
<212> TYPE: RNA
<213> ORGANISM: artificial
<220> FEATURE:
<223> OTHER INFORMATION: siRNA

<400> SEQUENCE: 21
agggccaaua aagccaugug a                                             21

<210> SEQ ID NO 22
<211> LENGTH: 21
<212> TYPE: RNA
<213> ORGANISM: artificial
<220> FEATURE:
<223> OTHER INFORMATION: siRNA

<400> SEQUENCE: 22
cuggcucuag gaccugaaga a                                             21

<210> SEQ ID NO 23
<211> LENGTH: 19
<212> TYPE: RNA
<213> ORGANISM: artificial
<220> FEATURE:
<223> OTHER INFORMATION: siRNA

<400> SEQUENCE: 23
gcaaauaggg cuucacaua                                                19

<210> SEQ ID NO 24
<211> LENGTH: 19
<212> TYPE: RNA
<213> ORGANISM: artificial
<220> FEATURE:
<223> OTHER INFORMATION: siRNA

<400> SEQUENCE: 24
aggcucagcu uguguguaa                                                19

<210> SEQ ID NO 25
<211> LENGTH: 19
<212> TYPE: RNA
<213> ORGANISM: artificial
<220> FEATURE:
<223> OTHER INFORMATION: siRNA

<400> SEQUENCE: 25
ggacgaggga ccuugcauu                                                19

<210> SEQ ID NO 26
<211> LENGTH: 19
<212> TYPE: RNA
<213> ORGANISM: artificial
<220> FEATURE:
<223> OTHER INFORMATION: siRNA

<400> SEQUENCE: 26
cagcuagagu ccagagguu                                                19

<210> SEQ ID NO 27

```
<211> LENGTH: 19
<212> TYPE: RNA
<213> ORGANISM: artificial
<220> FEATURE:
<223> OTHER INFORMATION: siRNA

<400> SEQUENCE: 27
gcacagcaac gcaaccuca                                                19

<210> SEQ ID NO 28
<211> LENGTH: 19
<212> TYPE: RNA
<213> ORGANISM: artificial
<220> FEATURE:
<223> OTHER INFORMATION: siRNA

<400> SEQUENCE: 28
gagcuucggu gacaaccug                                                19

<210> SEQ ID NO 29
<211> LENGTH: 19
<212> TYPE: RNA
<213> ORGANISM: artificial
<220> FEATURE:
<223> OTHER INFORMATION: siRNA

<400> SEQUENCE: 29
ugaucaucgu ggugcagaa                                                19

<210> SEQ ID NO 30
<211> LENGTH: 19
<212> TYPE: RNA
<213> ORGANISM: artificial
<220> FEATURE:
<223> OTHER INFORMATION: siRNA

<400> SEQUENCE: 30
gaccaucgac cguuucucu                                                19

<210> SEQ ID NO 31
<211> LENGTH: 19
<212> TYPE: RNA
<213> ORGANISM: artificial
<220> FEATURE:
<223> OTHER INFORMATION: siRNA

<400> SEQUENCE: 31
gcacaaggug uacgcgcuc                                                19

<210> SEQ ID NO 32
<211> LENGTH: 19
<212> TYPE: RNA
<213> ORGANISM: artificial
<220> FEATURE:
<223> OTHER INFORMATION: siRNA

<400> SEQUENCE: 32
caacuuccgc ugcgcacug                                                19

<210> SEQ ID NO 33
<211> LENGTH: 19
<212> TYPE: RNA
<213> ORGANISM: artificial
<220> FEATURE:
<223> OTHER INFORMATION: siRNA

<400> SEQUENCE: 33
```
gcgcgcaucu ucaaggccu                                                19

<210> SEQ ID NO 34
<211> LENGTH: 19
<212> TYPE: RNA
<213> ORGANISM: artificial
<220> FEATURE:
<223> OTHER INFORMATION: siRNA

<400> SEQUENCE: 34
caggcacgga ccagacuga                                                19

<210> SEQ ID NO 35
<211> LENGTH: 19
<212> TYPE: RNA
<213> ORGANISM: artificial
<220> FEATURE:
<223> OTHER INFORMATION: siRNA

<400> SEQUENCE: 35
gagcggaccu uauggcuac                                                19

<210> SEQ ID NO 36
<211> LENGTH: 19
<212> TYPE: RNA
<213> ORGANISM: artificial
<220> FEATURE:
<223> OTHER INFORMATION: siRNA

<400> SEQUENCE: 36
gaacaggugg cacagcuua                                                19

<210> SEQ ID NO 37
<211> LENGTH: 19
<212> TYPE: RNA
<213> ORGANISM: artificial
<220> FEATURE:
<223> OTHER INFORMATION: siRNA

<400> SEQUENCE: 37
gaaacgaccu ucuaugacg                                                19

<210> SEQ ID NO 38
<211> LENGTH: 19
<212> TYPE: RNA
<213> ORGANISM: artificial
<220> FEATURE:
<223> OTHER INFORMATION: siRNA

<400> SEQUENCE: 38
ugaaagcuca gaacucgga                                                19

<210> SEQ ID NO 39
<211> LENGTH: 19
<212> TYPE: RNA
<213> ORGANISM: artificial
<220> FEATURE:
<223> OTHER INFORMATION: siRNA

<400> SEQUENCE: 39
acggaacucu ugugcguaa                                                19

<210> SEQ ID NO 40
<211> LENGTH: 19
<212> TYPE: RNA

```
<213> ORGANISM: artificial
<220> FEATURE:
<223> OTHER INFORMATION: siRNA

<400> SEQUENCE: 40
gaacacacaa cgucuugga                                               19

<210> SEQ ID NO 41
<211> LENGTH: 19
<212> TYPE: RNA
<213> ORGANISM: artificial
<220> FEATURE:
<223> OTHER INFORMATION: siRNA

<400> SEQUENCE: 41
aacguuagcu ucaccaaca                                               19

<210> SEQ ID NO 42
<211> LENGTH: 19
<212> TYPE: RNA
<213> ORGANISM: artificial
<220> FEATURE:
<223> OTHER INFORMATION: siRNA

<400> SEQUENCE: 42
cgauguuguu ucuguggaa                                               19

<210> SEQ ID NO 43
<211> LENGTH: 19
<212> TYPE: RNA
<213> ORGANISM: artificial
<220> FEATURE:
<223> OTHER INFORMATION: siRNA

<400> SEQUENCE: 43
caacaggaau gcagcagug                                               19

<210> SEQ ID NO 44
<211> LENGTH: 19
<212> TYPE: RNA
<213> ORGANISM: artificial
<220> FEATURE:
<223> OTHER INFORMATION: siRNA

<400> SEQUENCE: 44
gaguucgccu ucaauauga                                               19

<210> SEQ ID NO 45
<211> LENGTH: 19
<212> TYPE: RNA
<213> ORGANISM: artificial
<220> FEATURE:
<223> OTHER INFORMATION: siRNA

<400> SEQUENCE: 45
ggacgcaggu ucuccaaac                                               19

<210> SEQ ID NO 46
<211> LENGTH: 19
<212> TYPE: RNA
<213> ORGANISM: artificial
<220> FEATURE:
<223> OTHER INFORMATION: siRNA

<400> SEQUENCE: 46
uuagagacau caaguaugg                                               19
```

<210> SEQ ID NO 47
<211> LENGTH: 19
<212> TYPE: RNA
<213> ORGANISM: artificial
<220> FEATURE:
<223> OTHER INFORMATION: siRNA

<400> SEQUENCE: 47
gcaauugaaa guuugguaa                                                    19

<210> SEQ ID NO 48
<211> LENGTH: 19
<212> TYPE: RNA
<213> ORGANISM: artificial
<220> FEATURE:
<223> OTHER INFORMATION: siRNA

<400> SEQUENCE: 48
cccacaaccu uuagacuga                                                    19

<210> SEQ ID NO 49
<211> LENGTH: 19
<212> TYPE: RNA
<213> ORGANISM: artificial
<220> FEATURE:
<223> OTHER INFORMATION: siRNA

<400> SEQUENCE: 49
gaauccauau cacuacgaa                                                    19

<210> SEQ ID NO 50
<211> LENGTH: 19
<212> TYPE: RNA
<213> ORGANISM: artificial
<220> FEATURE:
<223> OTHER INFORMATION: siRNA

<400> SEQUENCE: 50
guacagaguu acuacuuag                                                    19

<210> SEQ ID NO 51
<211> LENGTH: 19
<212> TYPE: RNA
<213> ORGANISM: artificial
<220> FEATURE:
<223> OTHER INFORMATION: siRNA

<400> SEQUENCE: 51
ggaacaaccc gucuacaca                                                    19

<210> SEQ ID NO 52
<211> LENGTH: 19
<212> TYPE: RNA
<213> ORGANISM: artificial
<220> FEATURE:
<223> OTHER INFORMATION: siRNA

<400> SEQUENCE: 52
gaacaagccg cacgucaag                                                    19

<210> SEQ ID NO 53
<211> LENGTH: 19
<212> TYPE: RNA
<213> ORGANISM: artificial
<220> FEATURE:

<223> OTHER INFORMATION: siRNA

<400> SEQUENCE: 53
gaccuucgau gucaacgag                      19

<210> SEQ ID NO 54
<211> LENGTH: 19
<212> TYPE: RNA
<213> ORGANISM: artificial
<220> FEATURE:
<223> OTHER INFORMATION: siRNA

<400> SEQUENCE: 54
ggaagucggu gaagaacgg                      19

<210> SEQ ID NO 55
<211> LENGTH: 19
<212> TYPE: RNA
<213> ORGANISM: artificial
<220> FEATURE:
<223> OTHER INFORMATION: siRNA

<400> SEQUENCE: 55
ugagacaggc cauguguau                      19

<210> SEQ ID NO 56
<211> LENGTH: 19
<212> TYPE: RNA
<213> ORGANISM: artificial
<220> FEATURE:
<223> OTHER INFORMATION: siRNA

<400> SEQUENCE: 56
ggacugugcu gaagaguac                      19

<210> SEQ ID NO 57
<211> LENGTH: 19
<212> TYPE: RNA
<213> ORGANISM: artificial
<220> FEATURE:
<223> OTHER INFORMATION: siRNA

<400> SEQUENCE: 57
gcaccaagag ugaaugauc                      19

<210> SEQ ID NO 58
<211> LENGTH: 19
<212> TYPE: RNA
<213> ORGANISM: artificial
<220> FEATURE:
<223> OTHER INFORMATION: siRNA

<400> SEQUENCE: 58
gcaccagugu cugcuagug                      19

<210> SEQ ID NO 59
<211> LENGTH: 19
<212> TYPE: RNA
<213> ORGANISM: artificial
<220> FEATURE:
<223> OTHER INFORMATION: siRNA

<400> SEQUENCE: 59
gcacgauggg cucagcuuu                      19

```
<210> SEQ ID NO 60
<211> LENGTH: 19
<212> TYPE: RNA
<213> ORGANISM: artificial
<220> FEATURE:
<223> OTHER INFORMATION: siRNA

<400> SEQUENCE: 60
cuacgaacau gacccuauc                                                  19

<210> SEQ ID NO 61
<211> LENGTH: 19
<212> TYPE: RNA
<213> ORGANISM: artificial
<220> FEATURE:
<223> OTHER INFORMATION: siRNA

<400> SEQUENCE: 61
gaaccugacu uccaugcgg                                                  19

<210> SEQ ID NO 62
<211> LENGTH: 19
<212> TYPE: RNA
<213> ORGANISM: artificial
<220> FEATURE:
<223> OTHER INFORMATION: siRNA

<400> SEQUENCE: 62
agaaagagcu ugacaguaa                                                  19

<210> SEQ ID NO 63
<211> LENGTH: 19
<212> TYPE: RNA
<213> ORGANISM: artificial
<220> FEATURE:
<223> OTHER INFORMATION: siRNA

<400> SEQUENCE: 63
gaacuaaacu aucagguaa                                                  19

<210> SEQ ID NO 64
<211> LENGTH: 19
<212> TYPE: RNA
<213> ORGANISM: artificial
<220> FEATURE:
<223> OTHER INFORMATION: siRNA

<400> SEQUENCE: 64
gcauguagcu gugguuauu                                                  19

<210> SEQ ID NO 65
<211> LENGTH: 19
<212> TYPE: RNA
<213> ORGANISM: artificial
<220> FEATURE:
<223> OTHER INFORMATION: siRNA

<400> SEQUENCE: 65
caaucuagcu acagugaug                                                  19

<210> SEQ ID NO 66
<211> LENGTH: 19
<212> TYPE: RNA
<213> ORGANISM: artificial
<220> FEATURE:
<223> OTHER INFORMATION: siRNA
```

```
<400> SEQUENCE: 66
cugcgagacu acaaaguua                                                    19

<210> SEQ ID NO 67
<211> LENGTH: 19
<212> TYPE: RNA
<213> ORGANISM: artificial
<220> FEATURE:
<223> OTHER INFORMATION: siRNA

<400> SEQUENCE: 67
gcacuugcuu cgaucuauu                                                    19

<210> SEQ ID NO 68
<211> LENGTH: 19
<212> TYPE: RNA
<213> ORGANISM: artificial
<220> FEATURE:
<223> OTHER INFORMATION: siRNA

<400> SEQUENCE: 68
gacaaagagc ugagugauu                                                    19

<210> SEQ ID NO 69
<211> LENGTH: 19
<212> TYPE: RNA
<213> ORGANISM: artificial
<220> FEATURE:
<223> OTHER INFORMATION: siRNA

<400> SEQUENCE: 69
gcacagcugu uuggucuag                                                    19

<210> SEQ ID NO 70
<211> LENGTH: 19
<212> TYPE: RNA
<213> ORGANISM: artificial
<220> FEATURE:
<223> OTHER INFORMATION: siRNA

<400> SEQUENCE: 70
caacgggaca gacaguaua                                                    19

<210> SEQ ID NO 71
<211> LENGTH: 19
<212> TYPE: RNA
<213> ORGANISM: artificial
<220> FEATURE:
<223> OTHER INFORMATION: siRNA

<400> SEQUENCE: 71
gcaagacggg agcgaguaa                                                    19

<210> SEQ ID NO 72
<211> LENGTH: 19
<212> TYPE: RNA
<213> ORGANISM: artificial
<220> FEATURE:
<223> OTHER INFORMATION: siRNA

<400> SEQUENCE: 72
ggagggacaa gaucaacaa                                                    19

<210> SEQ ID NO 73
<211> LENGTH: 19
```

```
<212> TYPE: RNA
<213> ORGANISM: artificial
<220> FEATURE:
<223> OTHER INFORMATION: siRNA

<400> SEQUENCE: 73
gaagagccca gcacaacga                                                      19

<210> SEQ ID NO 74
<211> LENGTH: 19
<212> TYPE: RNA
<213> ORGANISM: artificial
<220> FEATURE:
<223> OTHER INFORMATION: siRNA

<400> SEQUENCE: 74
caaaaucccu ucagcaaug                                                      19
```